(12) United States Patent
Angibaud et al.

(10) Patent No.: US 8,529,629 B2
(45) Date of Patent: *Sep. 10, 2013

(54) SHOULDER PROSTHESIS WITH HUMERAL FRACTURE STEM

(75) Inventors: Laurent Angibaud, Ponson-Dessus (FR); Pierre-Henri Flurin, Le Bouscat (FR)

(73) Assignee: Exactech, Inc., Gainesville, FL (US)

(*) Notice: Subject to any disclaimer, the term of this patent is extended or adjusted under 35 U.S.C. 154(b) by 824 days.

This patent is subject to a terminal disclaimer.

(21) Appl. No.: 12/493,475

(22) Filed: Jun. 29, 2009

(65) Prior Publication Data

US 2009/0265010 A1 Oct. 22, 2009

Related U.S. Application Data

(63) Continuation of application No. 10/953,131, filed on Sep. 29, 2004, now Pat. No. 7,556,652.

(60) Provisional application No. 60/542,001, filed on Feb. 5, 2004, provisional application No. 60/581,397, filed on Jun. 21, 2004.

(51) Int. Cl.
*A61F 2/40* (2006.01)

(52) U.S. Cl.
USPC ...................................................... 623/19.14

(58) Field of Classification Search
CPC ....................................................... A61F 2/44
USPC .................. 623/19.11–19.14, 23.26, 23.28, 623/23.31, 23.35, 23.44, 23.46; 606/62–68
See application file for complete search history.

(56) References Cited

U.S. PATENT DOCUMENTS

| | | | | |
|---|---|---|---|---|
| 2,136,471 | A | * | 11/1938 | Schneider ...................... 606/62 |
| 5,282,865 | A | | 2/1994 | Dong |
| 5,489,309 | A | | 2/1996 | Lackey et al. |
| 5,944,758 | A | | 8/1999 | Mansat et al. |
| 5,961,555 | A | | 10/1999 | Huebner |
| 6,102,953 | A | | 8/2000 | Huebner |
| 6,168,627 | B1 | | 1/2001 | Huebner |

(Continued)

FOREIGN PATENT DOCUMENTS

| EP | 0930858 | 7/1999 |
|---|---|---|
| EP | 1125565 | 8/2001 |

(Continued)

OTHER PUBLICATIONS

"Fracture Humeral Stem-Patent"; Subject: "The Purpose of this Document is to Define the Background of the Invention, the Summary of the Invention and a Description of Preferred Embodiment"; Nov. 28, 2003; From: L.Angibaud; To: G.Miller, R.Cloutier & C.Roche.

(Continued)

*Primary Examiner* — Pedro Philogene
*Assistant Examiner* — David Comstock
(74) *Attorney, Agent, or Firm* — Greenberg Traurig, LLP

(57) ABSTRACT

Various embodiments of the present invention are directed to a shoulder prosthesis. These embodiments may relate to a shoulder prosthesis including, for example, a humeral stem for fracture indication. Of note, certain embodiments of the present invention provide a humeral prosthesis with improved integration of the tuberosities around the humeral stem. Various methods relating to uses and applications of the prosthesis are also disclosed.

34 Claims, 25 Drawing Sheets

(56) References Cited

U.S. PATENT DOCUMENTS

| | | |
|---|---|---|
| 6,168,628 B1 | 1/2001 | Huebner |
| 6,171,341 B1 | 1/2001 | Boileau |
| 6,193,758 B1 | 2/2001 | Huebner |
| 6,334,874 B1 | 1/2002 | Tornier et al. |
| 6,398,812 B1 | 6/2002 | Masini |
| 6,436,144 B1 | 8/2002 | Ahrens |
| 6,494,913 B1 | 12/2002 | Huebner |
| 6,520,994 B2 | 2/2003 | Nogarin |
| 6,620,197 B2 | 9/2003 | Maroney et al. |
| 2001/0037152 A1 | 11/2001 | Rockwood, Jr. |
| 2003/0014119 A1 | 1/2003 | Capon et al. |
| 2004/0034431 A1 | 2/2004 | Maroney et al. |

FOREIGN PATENT DOCUMENTS

| | | |
|---|---|---|
| FR | 2689758 | 10/1993 |
| FR | 2763501 | 11/1998 |
| FR | 2826256 | 12/2002 |
| WO | 9522302 | 8/1995 |
| WO | 9815241 | 4/1998 |

OTHER PUBLICATIONS

English language abstract of FR2763501 from the esp@cenet database.

English language abstract of FR2689758 from the esp@cenet database.

* cited by examiner

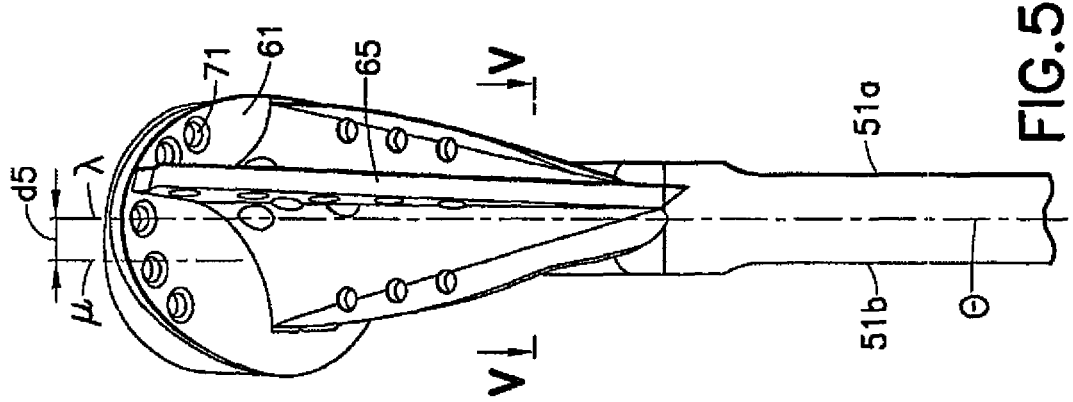
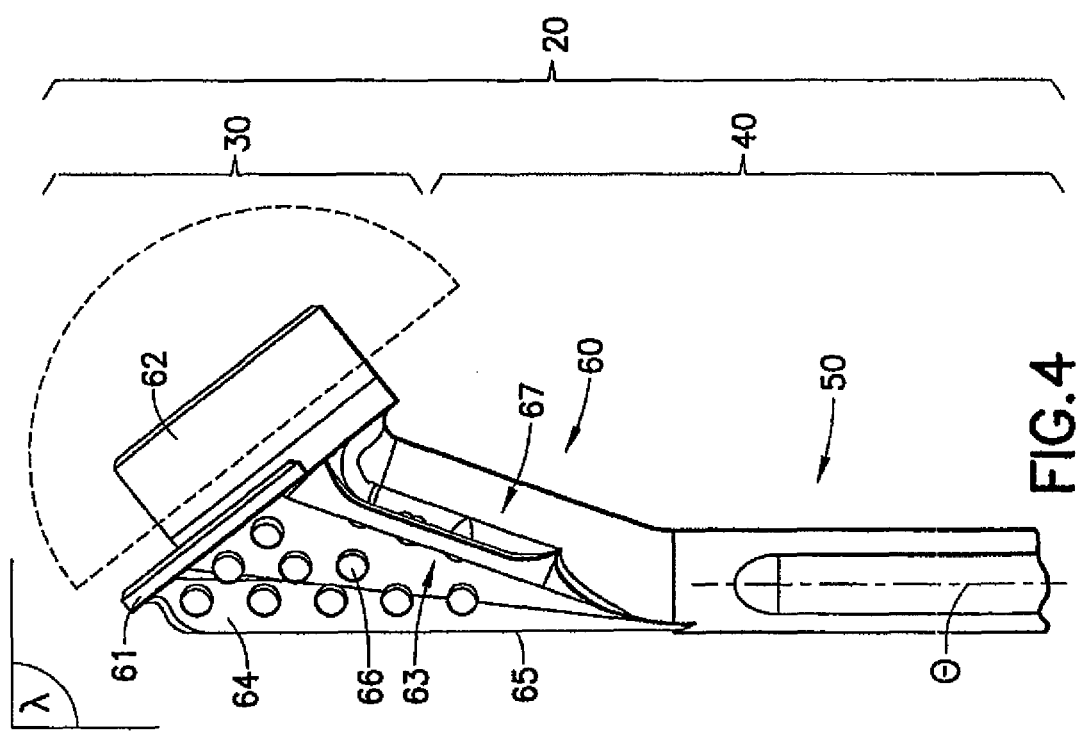

SHOULDER PROSTHESIS WITH HUMERAL FRACTURE STEM

CROSS-REFERENCE TO RELATED APPLICATIONS

This application is a continuation of U.S. application Ser. No. 10/953,131, filed Sep. 29, 2004 now U.S. Pat. No. 7,556,652, which claims the benefit under 35 U.S.C. 119(e) of U.S. Provisional Application Ser. No. 60/542,001, filed Feb. 5, 2004 and U.S. Provisional Application Ser. No. 60/581,397, filed Jun. 21, 2004. Each of the aforementioned applications is incorporated herein by reference in its entirety.

FIELD OF THE INVENTION

Various embodiments of the present invention are directed to a shoulder prosthesis. These embodiments may relate to a shoulder prosthesis including, for example, a humeral stem for fracture indication.

Of note, certain embodiments of the present invention provide a humeral prosthesis with improved integration of the tuberosities around the humeral stem.

Various methods relating to uses and applications of the prosthesis are also disclosed.

BACKGROUND OF THE INVENTION

When the upper extremity of the humerus is fractured, the humerus generally breaks into several pieces, in particular the humeral head, the lesser tuberosity, the greater tuberosity and the humerus shaft. This type of fracture is known as a "four part humeral fracture". In this case, as there is no blood supply to the humeral head by the tuberosities, a necrosis of the humeral head occurs. Shoulder prosthesis may be used: the anatomical head of the humerus is replaced by an approximately hemispheric prosthetic humeral head; while the other fractured pieces may be set around the humeral stem.

Examples of various patent documents in the shoulder prosthesis area include the following:

U.S. Pat. No. 5,282,865 to Dong relates to a modular humeral shoulder prosthesis for implant in a predetermined position in the natural humerus to replace the natural humeral head of a shoulder joint. The prosthetic implant has a humeral head component including a humeral head member with a spherical bearing surface of predetermined radius extending from an origin to the bearing surface, an undersurface extending in a first direction, an elongate post integral with and projecting in a given direction from the humeral head member, the given direction making a first acute angle with the first direction, and a post portion on the post, and a humeral stem component including a platform having an upper surface, a stem integral with and depending from the platform, the stem extending along a longitudinal axis for alignment generally longitudinally along the natural humerus, the upper surface extending in a second direction making a second acute angle with the longitudinal axis, and an elongate recess in the stem, the recess extending along the stem and including at least a recess portion complementary to the post portion for reception of the post portion within the recess portion in an integrated coupled assembly wherein the humeral head component is affixed to the humeral stem component with the undersurface of the humeral head member confronting the upper surface of the platform when the bearing surface is in the predetermined position to replace the natural humeral head.

U.S. Pat. No. 5,489,309 to Lackey et al. relates to a modular humeral prosthesis that can be custom fitted to a particular patient by interchanging sizes of the various components by a surgeon interoperatively. The prosthesis features a humeral head having a hemispherically shaped outer surface for placement within the glenoid cavity of a human scapula, the head including on its undersurface a recessed center portion having a first cooperating connecting means. The body has a proximal end and a distal end, with the proximal end including an angled platform having a second cooperating connecting means for engagement with said first connecting means, and the distal end having a third cooperating connecting means. The body also includes a plurality of fins. A cylindrical primary stem has a proximal end and a distal end, the proximal end having a forth cooperating connecting means for engagement with said third connecting means, and the distal end having a fifth cooperating connecting means. A cylindrical secondary stem has a proximal end and a distal end, the proximal end having a sixth cooperating connecting means for engagement with said fifth connecting means, and the distal end having a tip for insertion within the medullary canal of a resected human humerus.

U.S. Pat. No. 5,944,758 to Mansat et al. relates to a proximal humeral prosthesis that is designed for treating a fractured humerus. The prosthesis comprises a head corresponding to the humeral head of a patient, and a stem having a proximal end to which the head is mounted. The prosthesis has a central plane coincident with the longitudinal axis of the stem about which it has a mirror axis of symmetry. One, or preferably pair of, projecting ribs are positioned at or near the proximal end of the stem adjacent the head. The projecting ribs are offset in opposite directions relative to the center plane at substantially identical offset angles (e.g., about 20° to about 40°) approximating the greater or lesser tuberosity of the humerus. Also disclosed is a method of treating a fractured humerus with this prosthesis.

U.S. Pat. No. 5,961,555 to Huebner relates to a modular shoulder prosthesis including a head having a semi-spherical articulation surface bounded by an articular margin disposed in an articular plane generally normal to a head axis. The head further includes a backside disposed opposite the articulation surface and separated from the articulation surface by the articular margin. The prosthesis also includes a stem portion with a proximal end and a distal shaft for insertion into a medullary canal along a shaft axis. A coupling structure is adapted to removably attach the head to the stem through motion in the articular plane.

U.S. Pat. No. 6,102,953 to Huebner relates to a shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously determined position.

U.S. Pat. No. 6,168,627 to Huebner relates to a shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously determined position.

U.S. Pat. No. 6,168,628 to Huebner relates to a shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously determined position.

U.S. Pat. No. 6,171,341 to Boileau et al. relates to a humeral prosthesis of such a type that is provided with a rod intended to be anchored in the humeral canal of a patient, a metaphyseal element extending the rod upward and towards the inside, being this metaphyseal element attached at an area of connection to a flange that serves as support for a generally hemispheric cap capable of interacting with the shoulder socket. The area of connection is arranged approximately along a median line of the mentioned flange and the area of connection extends only over a portion of the mentioned median line so as to establish outside of the area of connection, or outside of a portion of the area of connection, a clearance zone for the joining and fusing of the osseous fragments of the metaphysis.

U.S. Pat. No. 6,193,758 to Huebner relates to a shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously-determined position.

U.S. Pat. No. 6,334,874 to Tornier et al. relates to a humeral prosthesis including a shaft adapted to be anchored in a medullary canal of humerus, a metaphyseal portion extending upwardly and endwardly from said shaft and being joined at its outer end to a flange which is adapted to support a dome to cooperate with a glenoidal cavity of a shoulder wherein the metaphyseal portion includes an inner part having at least one antero-posterior rib which is structured to provide an anatomical support for humeral tuberosities and which the at least one rib is oriented at an angle of between 45° to 135° with respect to a frontal plane of the prosthesis.

U.S. Pat. No. 6,398,812 to Masini relates to a humeral prosthesis with anatomic attachment areas for tendon or bone. In the preferred embodiment, at least one set of tendontone attachment points are provided along a line, at least a portion of which is divergent with respect to the axis of the stem. One or more sets of attachment points may be further be provided along a line which is substantially parallel to the axis of the stem, resulting in a "T" "L" or "U" shape. Alternatively, attachment points having a changing degree of diversion with respect to the axis of the stem may be provided along a common, curved line. The attachment points may simply be apertures formed through the body of the implant though, in the preferred embodiment, the apertures are provided on raised tabs. An area of bone-ingrowth material may be provided adjacent the attachment points, and may include a separate fastening mechanism such as a threaded hole to receive a screw. A groove may also be provided in any embodiment to receive the biceps tendon. Particularly with respect to fractures, including multi- and 'four-part' fractures, means specifically intended for the rigid reattachment of the greater or lesser tuberosities may be provided separately or in conjunction with other sets of reattachment configurations.

U.S. Pat. No. 6,436,144 to Ahrens relates to a shoulder joint endoprosthesis, consisting of a ball joint head and of a stem part which can be anchored in the humerus and has a prosthesis head. The prosthesis head has, on its outer surface, a multiplicity of bores into which pins for locking tubercle fragments can be driven with frictional fit and form fit.

U.S. Pat. No. 6,494,913 to Huebner relates to a system and method for installing a shoulder prosthesis. The method includes removing the original humeral head and shaping the proximal end of the humerus with one or more implements to prepare the humerus to receive the shoulder prosthesis.

U.S. Pat. No. 6,520,994 to Nogarin relates to a shoulder endoprosthesis for fractures of the upper end of the humerus, comprising a humeral stem, adapted to be accommodated in an intramedullary canal of the humerus and provided with multiple longitudinal ribs, and a humeral proximal part, which is suitable to couple to one end of the stem, is provided with a plurality of lateral fins and has, at an upper end, a portion for engagement with a humeral head which is suitable to reconstruct the head of the humerus of the patient.

Patent No. WO95/22302 in the name of Vincent et al. relates to a modular humeral prosthesis (1) for implantation into a humerus of a patient. A removable fracture cap (40) is provided with a shape so as to allow for space between the cap and the glenoid of a patient into whom the prosthesis is to be implanted. A removable humeral head (50) is provided and may be used interchangeably with the fracture cap depending on the condition of the patient's natural humeral head. Caps and heads of differing sizes may be disposed on the proximal humeral component. A modular distal stem extension (20) allows the overall length of the prosthesis to be selectively increased, thereby allowing the prosthesis to be fitted to patients having humeral shafts of differing sizes.

U.S. Patent Application Publication US2003/0014119 to Capon et al. relates to a shoulder prosthesis (5, 32) comprising a humerus rod (9, 39) intended to be introduced into the medullary cavity of a fractured humerus (2), and a roughly hemispherical head (12) which can be secured to the humerus rod and is designed to become lodged in a glene of the shoulder, characterized in that the humerus head (12) can be fixed to the humerus rod in any radial plane with respect to the axis of the humerus rod (9, 39) after the rod (9, 39) has been fixed into the humerus and the shoulder muscles have been fixed to the head.

French Application FR2763501 in the name of Patrick et al. relates to a shoulder prosthesis with modular components—an intramedullary shank (2) and two interchangeable heads (3,4). The shank has an upper end projection (6) and recess (7) which lie in line with the axis of the head after assembly. The projection has a series of equally-spaced peripheral protuberances (8), while the recess is coaxial with the projection, conical in shape and has a small angle of taper. One of the two heads has a central peg (21) and a cavity (22) shaped to engage with the recess and projection of the shank respectively. The other head has an offset peg and cavity which allow the head to be set in a number of different positions, according to the patient's morphology. In addition, the shank has a fin (16) on its outer surface, and its distal portion (2a) is coated with a porous material such as calcium hydroxyapatite, into which the bone cells can penetrate. Design simplicity, allowing more precise fit with smaller range of components.

French Application FR2689758 in the name of Lehuec et al. relates to a humeral shank for a shoulder prosthesis having a reinsertion finn (1a) on the outside of its proximal end, connected to the head by lengthwise and transverse sections which ensure the partial integration of the fin into the general volume defined by the body of the shank (1). The lengthwise connecting section is formed by grooves (1c) on either side of the fin, linking progressively with the body of the shank, while the transverse section is formed by cut-away surfaces designed to reduce the cross-section of the body at the level of the fin. The proximal end of the shank is also equipped with a thrust collar (1g) which is oval in shape, and has a hole (1f) pierced through it.

BRIEF DESCRIPTION OF THE DRAWINGS

FIG. 4 is a view of a humeral prosthesis according to an embodiment of the present, invention;

FIG. 5 is another view of the humeral prosthesis of FIG. 4;

Among those benefits and improvements that have been disclosed) other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
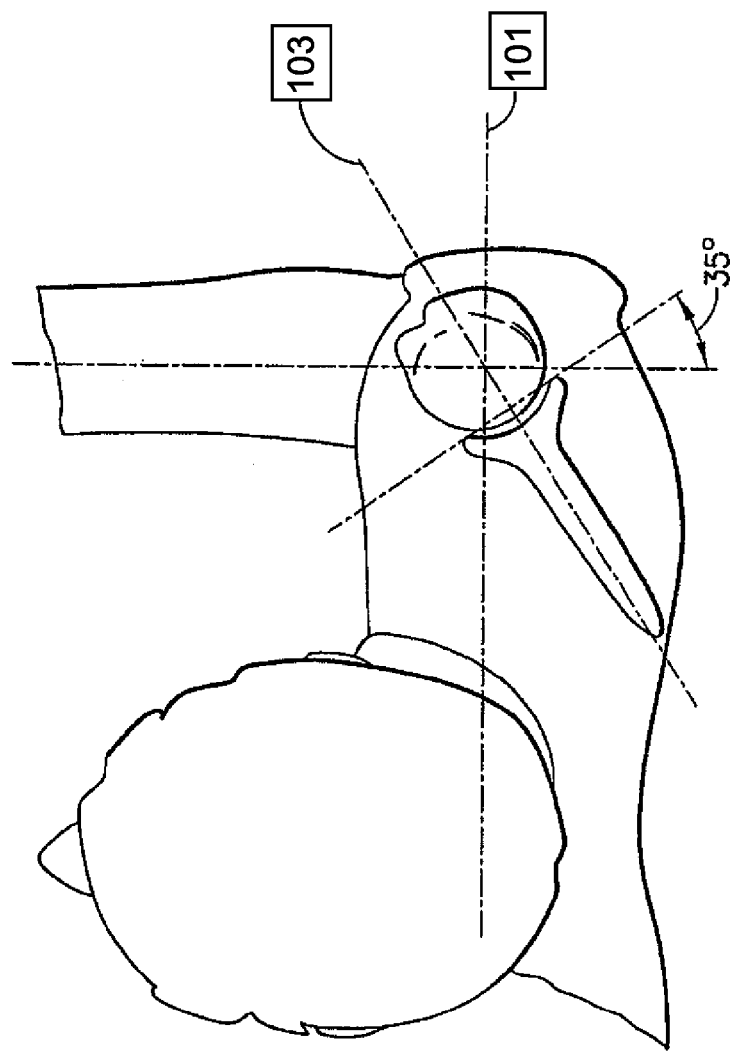
FIG. 1 shows a drawing in connection with defining a frontal plane of a prosthesis according to an embodiment of the present invention.

For the purposes of describing the present invention, the "frontal plane" of the prosthesis may refer, when the prosthesis is implanted in the body, to the plane which is substantially aligned with a frontal plane of the articular surface of the upper extremity of the humerus (i.e., the humeral head) 103, which frontal plane 103 of the articular surface of the upper extremity of the humerus is retroverted by approximately 35 degrees relative to a frontal plane of the body 101. In this regard, see FIG. 1 (it may be helpful, when discussing the frontal plane of the prosthesis, to envision a symmetric humeral stem, which is a particular case if the anterior offset of the anterior lateral fin is equal to 0 degrees—of course, the present invention is not limited to such a symmetric humeral stem).

In addition, for the purposes of describing the present invention, the "sagital plane" of the prosthesis may refer, when the prosthesis is implanted in the body, to a plane which is substantially 90 degrees offset from the frontal plane of the prosthesis.

A summary of one embodiment of the present invention will now be described. Under this embodiment a humeral prosthesis including a shaft intended to be anchored in the medullary canal of the humerus is provided. Further, a metaphyseal portion extending this shaft upwardly and inwardly is provided. This metaphyseal portion is joined to a flange supporting a prosthetic humeral head adapted to cooperate with the glenoid cavity of the shoulder. Of note, the metaphyseal portion may include, in its anterior-lateral side, a rib essentially at the level of the bicipital groove when the prosthesis is inserted with the correct retroversion. This rib may extend in a plane oriented at an angle with respect to the frontal plane of the prosthesis (in one example (which example is intended to be illustrative and not restrictive), the angle may be between about 0° and about 20° (inclusive)). The lateral edge of the anterior-lateral rib may be eccentered from the frontal plane of the prosthesis, which is called the anterior offset of the anterior-lateral rib, by a distance to be in relation (e.g., direct relation) with the bicipital groove. In one example (which example is intended to be illustrative and not restrictive), this offset from the frontal plane of the prosthesis to the lateral edge of the anterior-lateral rib may be between about 0 mm and about 13 mm (inclusive)). The offset may be essentially constant along the lateral edge course (or the offset may be non-constant along the lateral edge course).

Of note, the orientation and the dimension of the anterior-lateral rib in relation to the bicipital groove may aid in the suturing of the tuberosities against the anterior-lateral rib (and in a satisfactory configuration from an anatomical standpoint). In one specific example (which example is intended to be illustrative and not restrictive), the angle of orientation of the plane of the anterior-lateral rib with respect to the frontal plane of the prosthesis may be about 20° and the offset of the lateral edge of the anterior-lateral rib may be about 7 mm.

The anterior-lateral rib may include a window and/or one or more holes. Such window and/or hole(s) may aid osseous fusion through the anterior-lateral rib of the prosthesis.

The metaphyseal portion of the prosthesis may be defined, in its inner part, as a stem (e.g., to help ensure the mechanical stability and strength of the prosthesis). The stem of the metaphyseal portion of the prosthesis may have a cross section shaped, for example (which example is intended to be illustrative and not restrictive), like a portion of a circle or an ellipse. The curvature may be oriented medially while the flat line may be oriented laterally. In this embodiment, the frontal plane of the prosthesis could be defined as (or parallel to) the plane of symmetry of the inner shape (i.e., curve) of the metaphyseal portion. The lateral face of this metaphyseal portion may be provided, for example (which example is intended to be illustrative and not restrictive), with two ribs: one rib may be located in an anterior-medial position while the other rib may be located in a posterior-medial position. The width between the ribs may depend on the articular sector of the circular section and the radius of curvature.

In another example (which example is intended to be illustrative and not restrictive), the metaphyseal portion may be asymmetric (e.g., to better correspond to the anatomy of the proximal humerus). The anterior cavity created by the anterior-lateral rib and the anterior part of the metaphyseal portion may be shaped for the lesser tuberosity and the posterior cavity created by the anterior-lateral rib and the posterior part of the metaphyseal portion may be shaped for the greater tuberosity (this particularity may offer a unique asymmetric shape of the metaphyseal portion).

In another example (which example is intended to be illustrative and not restrictive), one or both of the above-mentioned cavities may be concave (this characteristic may allow for the conservation of more of the cancellous bone (as opposed to the amount of bone which needs to be removed with conventional designs).

Of note, a unique characteristic of this embodiment of the present invention may relate to a posterior offset in relation to the frontal plane of the prosthesis. In this regard, the morse taper, supporting the prosthetic humeral head and located on the flange, may be posteriorly eccentered from the frontal plane of the prosthesis by an offset. In one example (which example is intended to be illustrative and not restrictive), this offset may be between about 0 mm and about 4 mm (inclusive). In a more specific example (which example is intended to be illustrative and not restrictive), this offset may be about 2 mm.

Further, in one embodiment of the present invention one or more suture holes may be located on the flange (e.g., the upper extremity of the flange).

In contrast with certain conventional designs, the dimensions of the anterior-lateral rib according to an embodiment of the present invention may be unique for a rib of a shoulder prosthesis (this unique characteristic may come at least in part from the configuration of the metaphyseal portion of the present invention). Further, the inner part of metaphyseal portion of the present invention may be relatively strong (e.g., to ensure mechanical stability and strength), while the outer part may be relatively light and may essentially comprise a frame to reinsert the tuberosities into two cavities.

Figure 2:
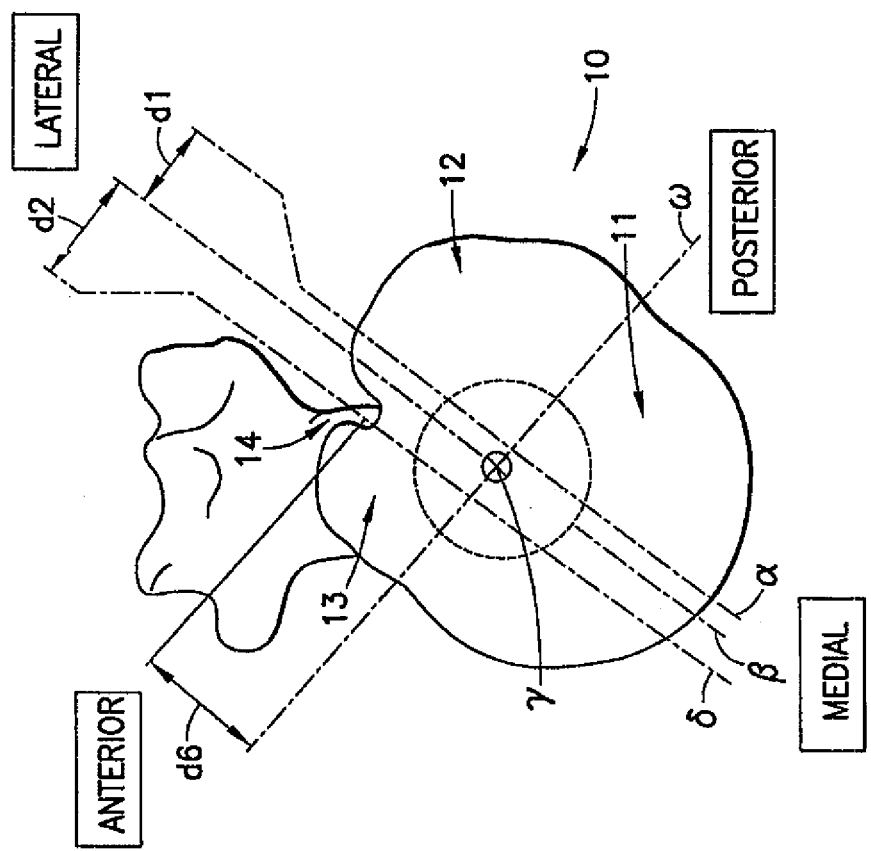
FIG. 2 shows the upper extremity of the humerus along the intra-medullary axis of the proximal humerus.
Figure 7:
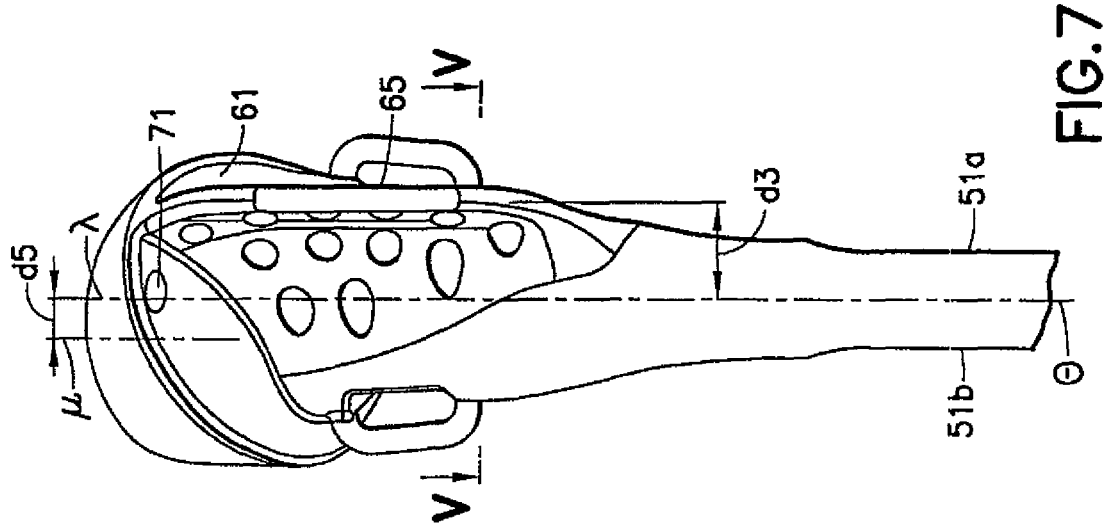
FIG. 7 is another view of the humeral prosthesis of FIG. 6.
Figure 6:
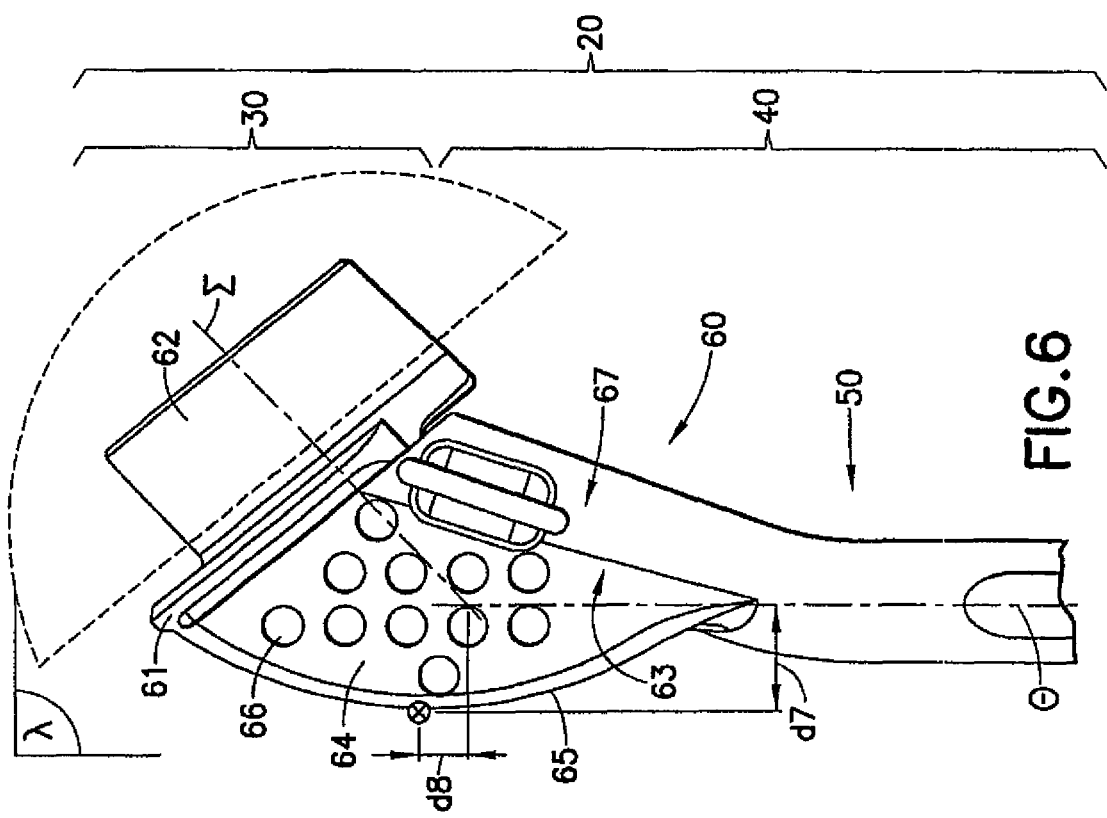
FIG. 6 is a view of a humeral prosthesis according to an embodiment of the present invention.
Figure 8:
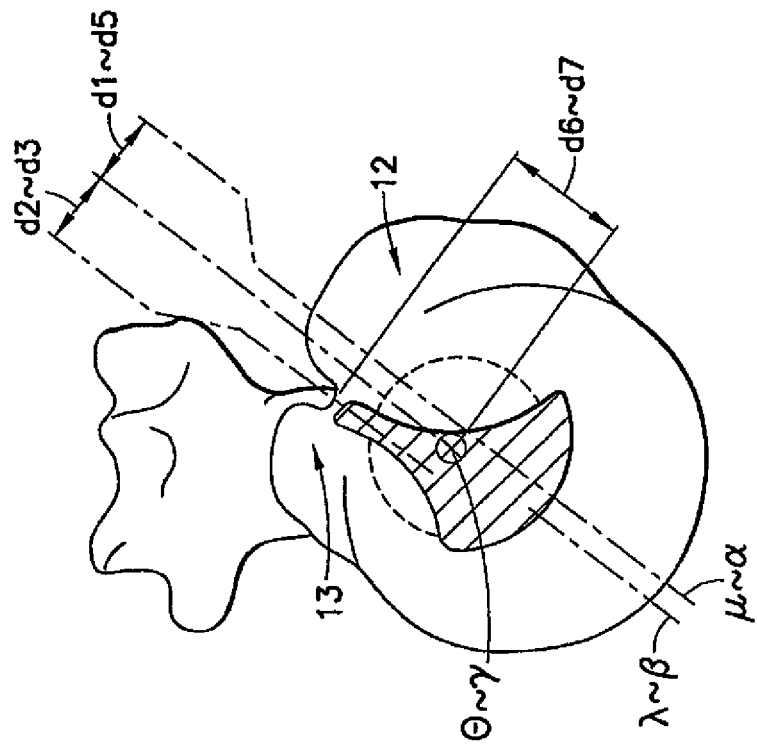
FIG. 8 is a section along line V-V of FIGS. 5 and 7.
Figure 9:
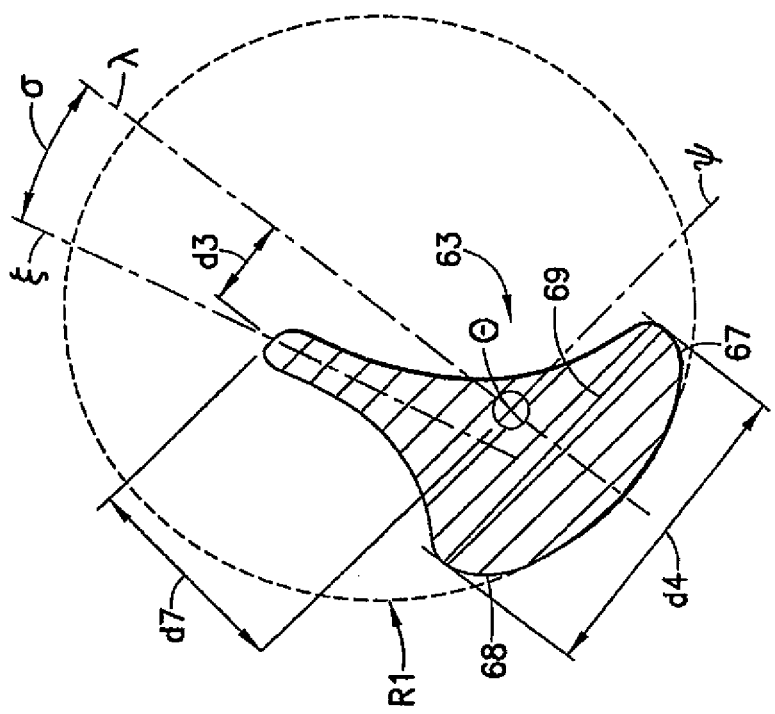
FIG. 9 is a view, similar to the view of FIG. 2, showing superimposed the section of the humeral prosthesis of FIGS. 4-7.

Referring now to FIG. 2, it is seen that this Fig. shows a typical proximal end to a humerus 10. Of note, the terms anterior, posterior, lateral and medial of the proximal humerus are defined by this FIG. 2 and the terms lower and upper used hereinafter must be understood as referring to a prosthesis borne by a patient standing-up. In any case, there is a rounded humeral head 11, which forms the actual joint with the scapula. Positioned around that humeral head 11 is the greater tuberosity 12 and the lesser tuberosity 13. Between the greater tuberosity 12 and the lesser tuberosity 13 is a groove 14 known as the bicipital groove. α denotes the equatorial plan of the humeral head. This axis may be determined according to a standardized protocol described in the article "On relevant morphometric parameters of the proximal humerus and misfit of standard prosthetic design" extracted from the publication "Journal of Shoulder and Elbow surgery" in the August 1999 issue. β denotes the plane parallel to α and passing through the intra-medullary axis γ of the humeral proximal cylinder 17 (see FIG. 3). The distance d1 between the plane α and the plane β is known as the posterior offset of the humeral head 11 (in relation to the intra-medullary axis of the proximal humerus γ). δ denotes the plane parallel to β and passing through the center of the bicipital groove 14. The distance d2 between the plane β and the plane δ is known as the anterior offset of the bicipital groove 14 (in relation to the intra-medullary axis of the proximal humerus γ). As can be seen from the above discussion, each plane α, β and δ is parallel with the medio-lateral axis of the proximal humerus. Ψ denotes the transepicondylar axis of the distal humerus, the angle a1 between the plane β and the axis Ψ (according an upper view) is known as the retroversion angle of the humeral head 11 relatively to the transepicondylar axis Ψ. For the following examples the orientation of the humeral prosthesis 20 respects the anatomical retroversion a1.

Figure 3:
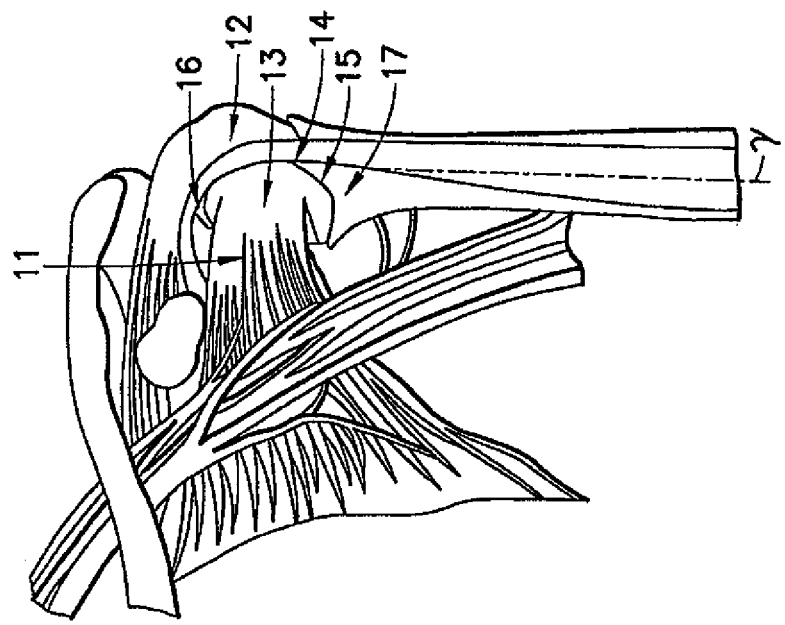
FIG. 3 shows the process of four-part fracture.

Referring now to FIG. 3, it is seen that this Fig. shows the privileged fracture lines when a four-part fracture occurs. More particularly, the humeral head 11 is separated from the greater tuberosity 12 and the lesser tuberosity 13 at the level of the anatomical neck 16. The greater tuberosity 12 and the lesser tuberosity 13 are separated from the proximal humerus shaft 17 at the level of the surgical neck 15. Laterally, the tuberosities 12 and 13 are separated at the level of the bicipital groove 14.

Referring now to FIGS. 4-9, it is seen that these Figs. show humeral prosthesis 20 according to certain embodiments of the present invention. More particularly, it is seen that humeral prosthesis 20 comprises a prosthetic humeral head 30 and a humeral stem 40. The humeral stem 40 comprises a shaft 50 (e.g., of substantially circular cross-section), intended to engage in the humerus shaft 17 (see FIG. 3) along the intra-medullary axis. Axis θ is the axis of revolution of the shaft 50. The shaft 50 may include two grooves 51a and 51b, which may be in essentially direct opposition (see FIGS. 5 and 7). One groove 51a may be in an anterior position while the other groove 51b may be in a posterior position.

A metaphyseal portion 60 may extend this shaft 50 upwardly and inwardly. This metaphyseal portion may be joined to a flange 61 supporting the prosthetic humeral head 30 (e.g., via a morse taper 62).

For the purposes of the discussion of the embodiments of these Figs., the frontal plane λ of the prosthesis may be the plane containing the central axis θ of the shaft 50. Moreover, the frontal plane λ may be the mirror plane between the groove 51a and the groove 51b and of the inner shape 68 of the metaphyseal portion 60. The frontal plane μ may be the plane of symmetry of the morse taper 62 and may be parallel to plane λ.

In use, the prosthesis 20 may be inserted along axis θ of the shaft 50 (i.e., along the intra-medullary axis γ of the humerus shaft 17 (see FIG. 3)). Further, the frontal plane λ of the prosthesis may be superposed with plane β of the humerus and plane μ may be superposed with plane α of the anatomic humeral head. This characteristic allows the respect of the anatomic parameters.

The metaphyseal portion 60 may comprise, in its outer face 63 an anterior-lateral rib 64. The anterior-lateral rib 64 may extend in a plane ξ oriented at an angle σ from the frontal plane λ. In one example (which example is intended to be illustrative and not restrictive), the anterior-lateral rib 64 may extend in a plane ξ of which the angle σ with respect to the frontal plane λ is between about 0° to about 20° (inclusive). In a more specific example (which example is intended to be illustrative and not restrictive), the angle σ may be 20°.

The free edge 65 of the anterior-lateral rib 64 may be eccentered from the frontal plane λ by a distance d3, which is the perpendicular projection of the free edge 65 to the frontal plane λ. In one example (which example is intended to be illustrative and not restrictive), the free edge 65 of the anterior-lateral rib 64 may be eccentered from the frontal plane λ by a value d3 between about 0 mm to about 13 mm (inclusive). In a more specific example (which example is intended to be illustrative and not restrictive), the free edge 65 of the anterior-lateral rib 64 may be eccentered from the frontal plane λ by a value d3 of about 7 mm. Of note, the distance d3 may be essentially the same as the distance d2 (this unique characteristic may allow the anatomical relocation of the lesser tuberosity 13 and the greater tuberosity 12 along the anterior-lateral rib 64 at the place of the original bicipital groove 14).

The anterior-lateral rib 64 may comprise (e.g., in its medial part) a plurality of holes 66. These holes 66 could be used, for example (which example is intended to be illustrative and not restrictive), for the following functions: (a) suture holes to secure the tuberosities 12 and/or 13 against the metaphyseal part 60; and/or (b) through these holes the tuberosities 12 and/or 13 could undergo fusion (i.e., the holes could aid in the formation of an osseous bridge ensuring efficient stability of the tuberosities 12 and/or 13).

The metaphyseal portion 60 of the prosthesis 20 may be defined in its inner part 67 as a stem to help ensure the mechanical property of the prosthesis 20. In one example (which example is intended to be illustrative and not restrictive), the inner part 67 may be symmetrical around the frontal plane $\lambda$. In another example (which example is intended to be illustrative and not restrictive), the section of the inner part 67 may be essentially represented by a part of a circle or an ellipse (wherein the internal edge 68 is the curvature R1 of the inner part oriented to the medial side and the external edge 69 is a virtual line oriented perpendicularly to the frontal plane $\lambda$) This virtual line 69 creates the boundary between the inner part 67 of the metaphyseal portion 60 and the outer part 63 of the metaphyseal portion 60.

In one example (which example is intended to be illustrative and not restrictive), the anterior-posterior width d4 of the inner part (i.e. length of the line 69) may be proportional to the height of the section. In a more specific example (which example is intended to be illustrative and not restrictive), the width d4 may be similar to the diameter of the shaft 50 at the level located between the shaft 50 and the metaphyseal portion 60 and the width d4 may be higher for an upper cross-section (this increasing of width d4 from distal to proximal may create a medial stop to help secure the tuberosities 12 and/or 13 in place).

Further, the flange 61 may include suture hole(s) 71 (e.g., on its upper extremity). These holes 71 may be used, for example (which example is intended to be illustrative and not restrictive), to perform a suture technique like a guy-wire, shrouds, and/or rigging.

Further still, the flange 61 supporting the morse taper 62 and the morse taper 62 supporting the prosthetic humeral head 30 may be posteriorly eccentered from the frontal plane $\lambda$. The frontal plane $\mu$ is the plane of symmetry of the morse taper 62, which is essentially parallel to the frontal plane $\lambda$ and may be posteriorly eccentered by an offset d5. In one example (which example is intended to be illustrative and not restrictive), the plane $\mu$ may be eccentered posteriorly from the frontal plane $\lambda$ by an offset d5 between about 0 mm to about 4 mm (inclusive). In a more specific example (which example is intended to be illustrative and not restrictive), the value of d5 may be about 2 mm. Of note, this unique characteristic may allow an anatomical location of the prosthetic humeral head 30 by respecting the notion of posterior offset of the humeral head. As a result, the distance d5 between the frontal plane $\lambda$ of the prosthesis and the plane $\mu$ may be approximately the same as the distance d1 between the equatorial plane $\alpha$ of the humeral head and the plane $\beta$.

Figure 10:
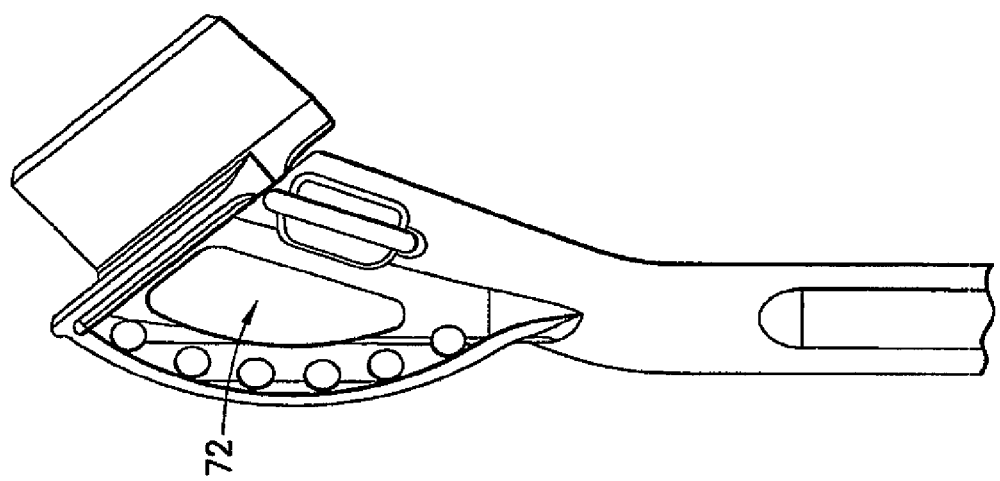
FIG. 10 is a view, similar to the view of FIG. 4, showing a prosthesis according to another embodiment of the present invention.
Figure 12:
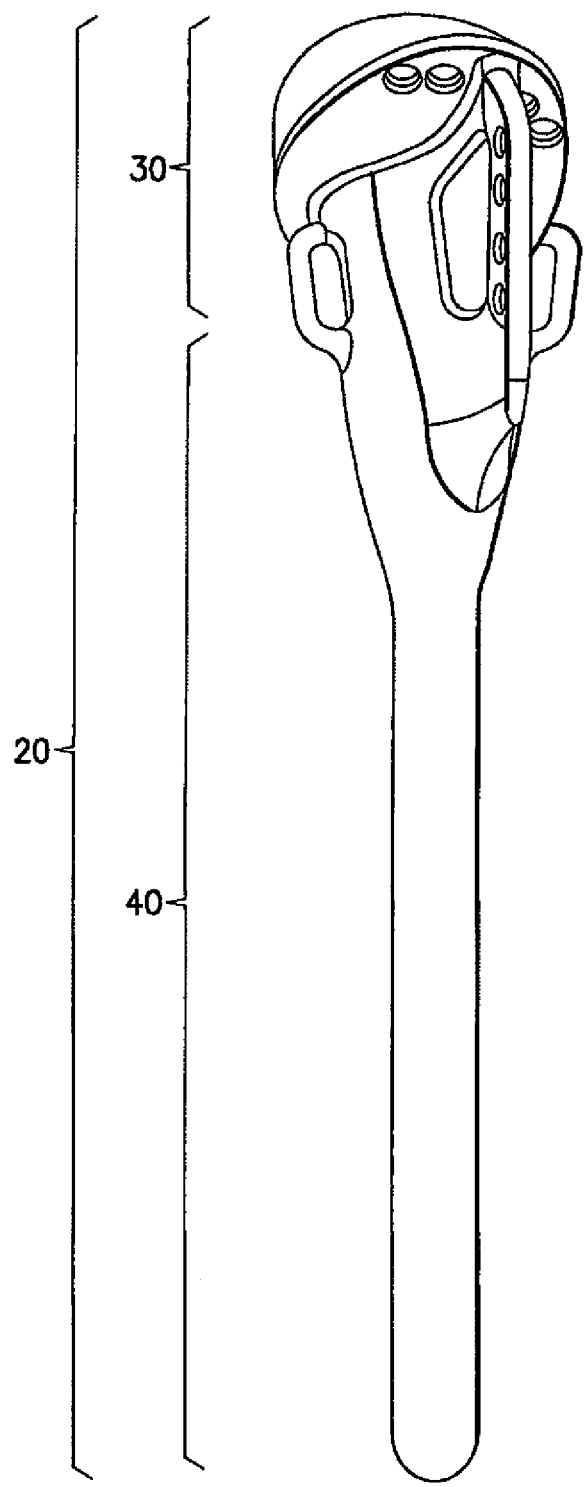
FIGS. 12-21 show additional views of various embodiments of a humeral prosthesis according to the present invention.
Figure 13:
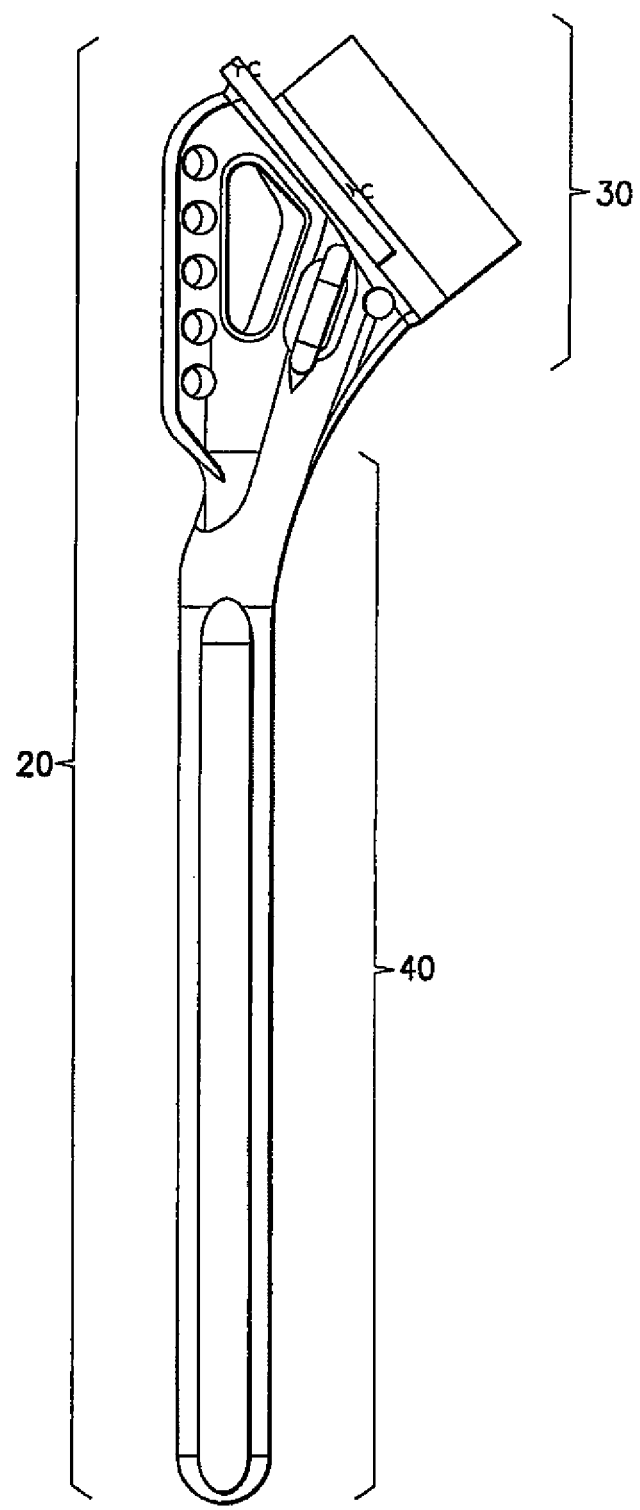
Figure 14:
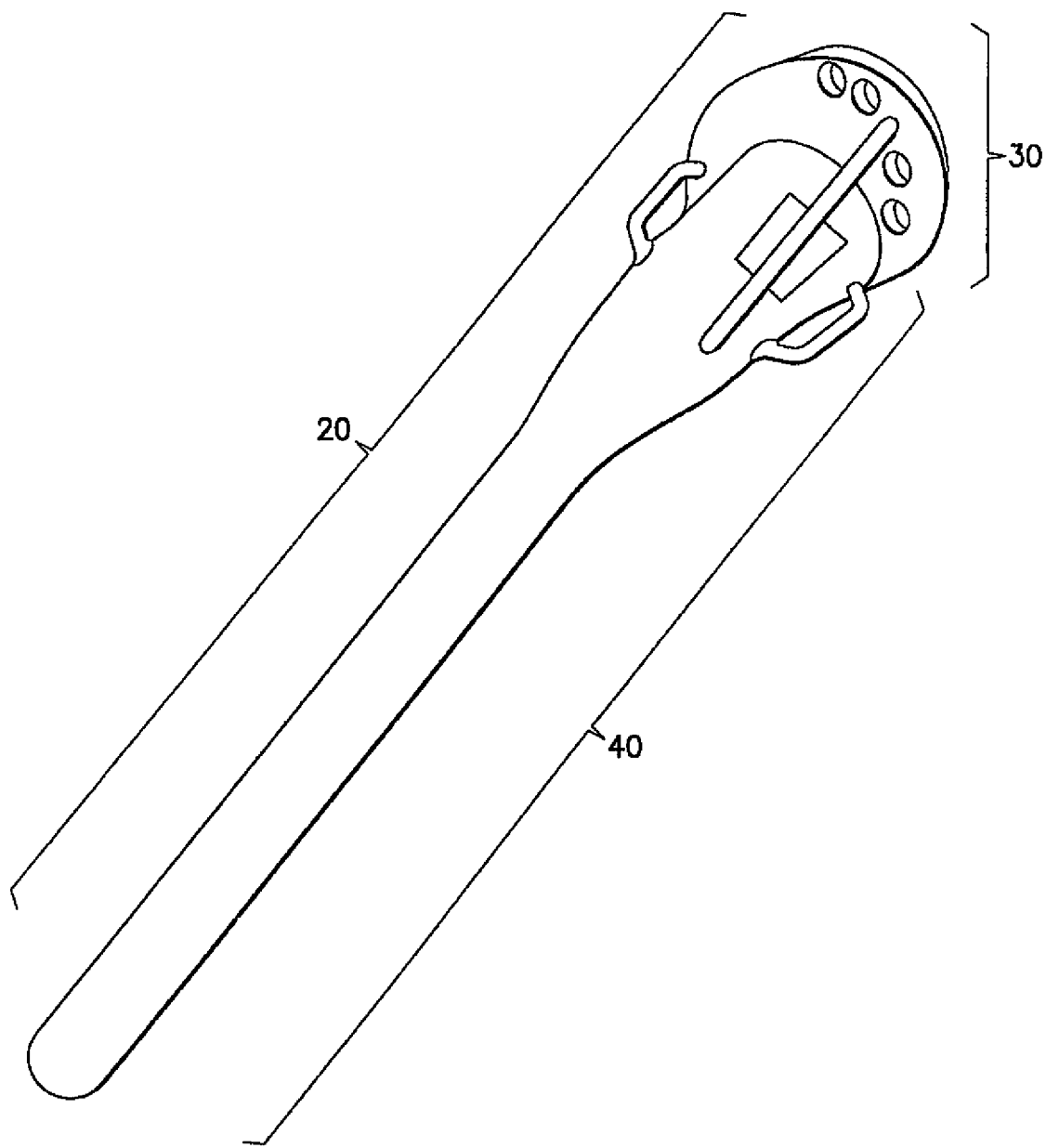
Figure 15:
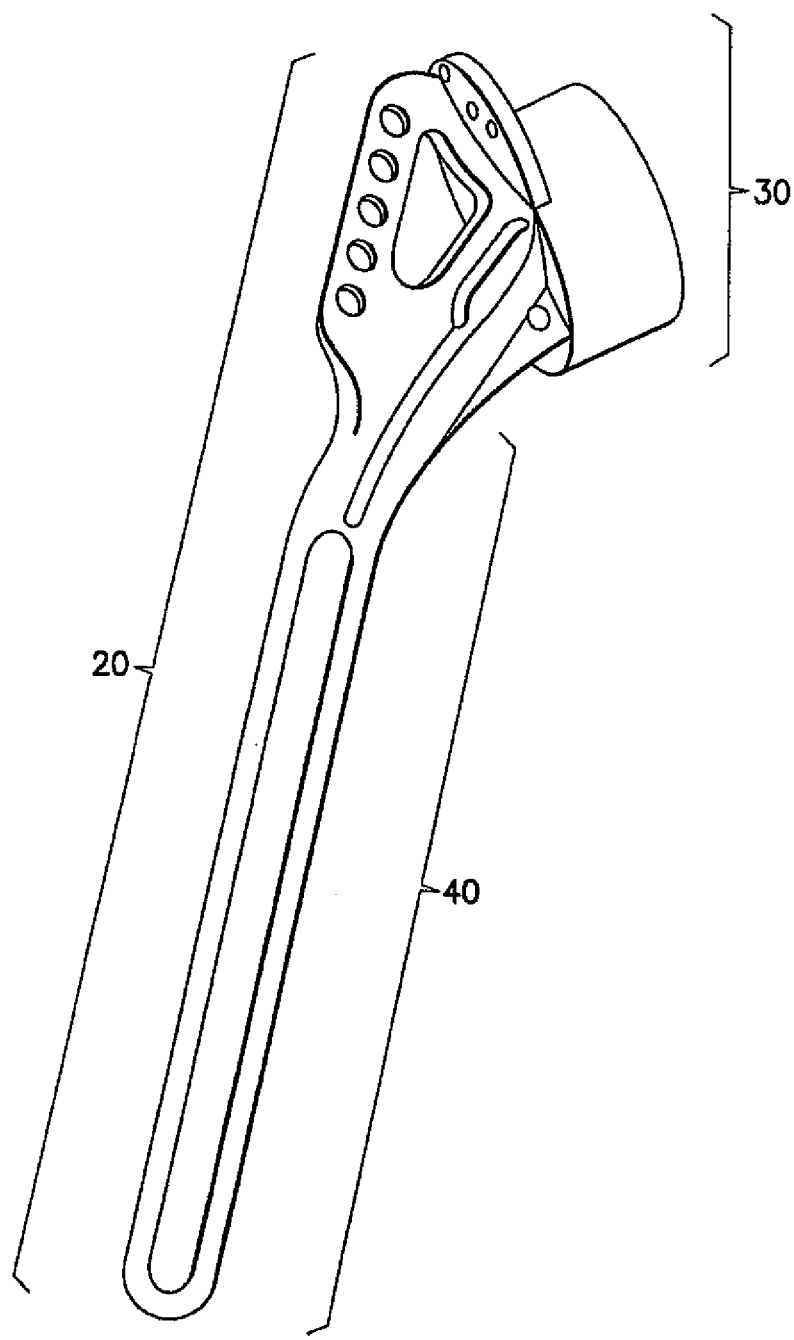
Figure 16:
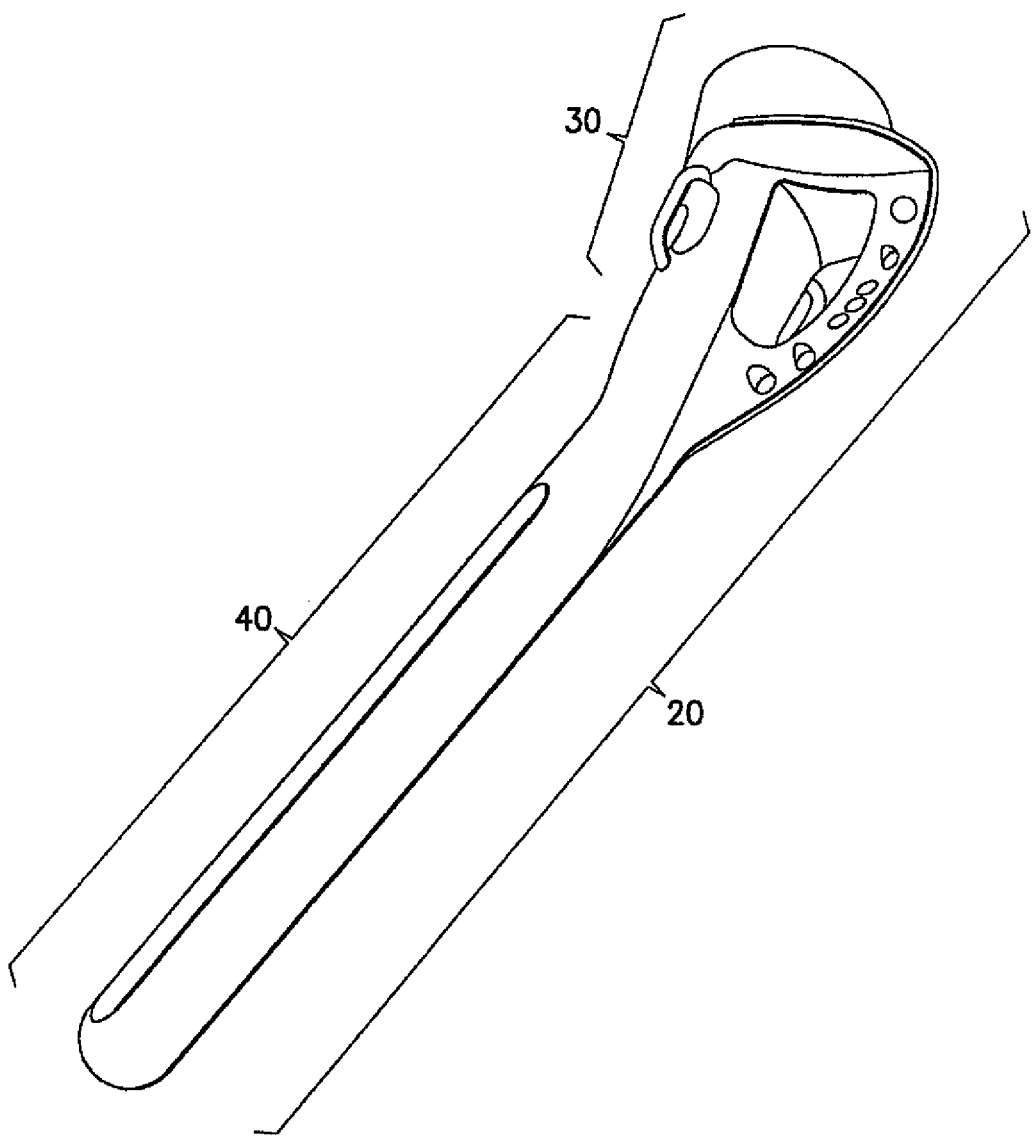
Figure 17:
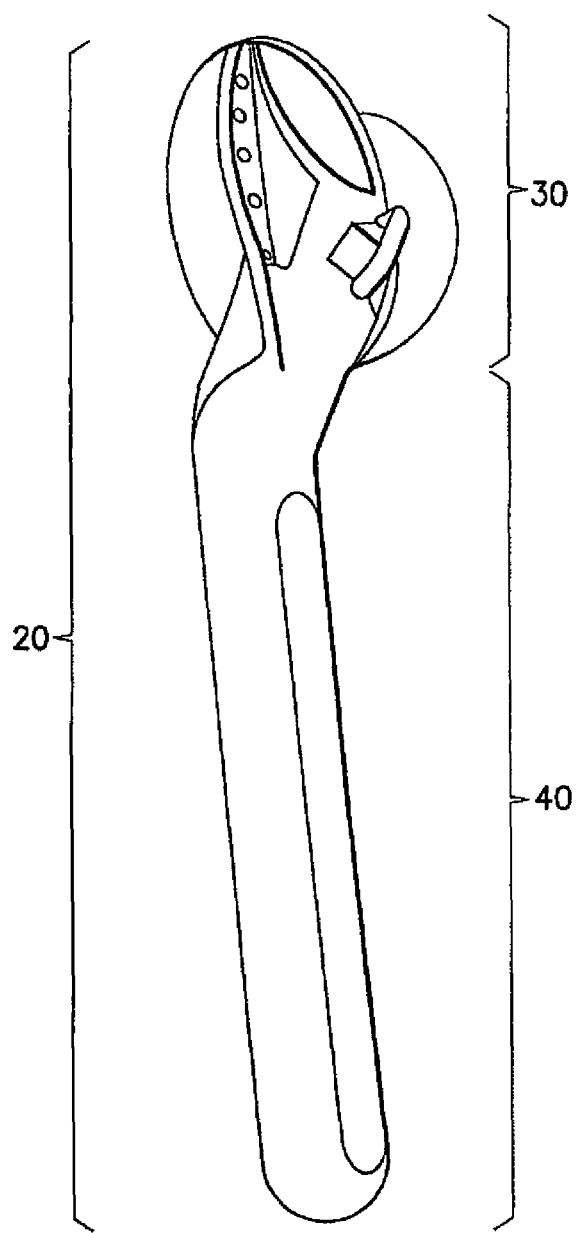
Figure 18:
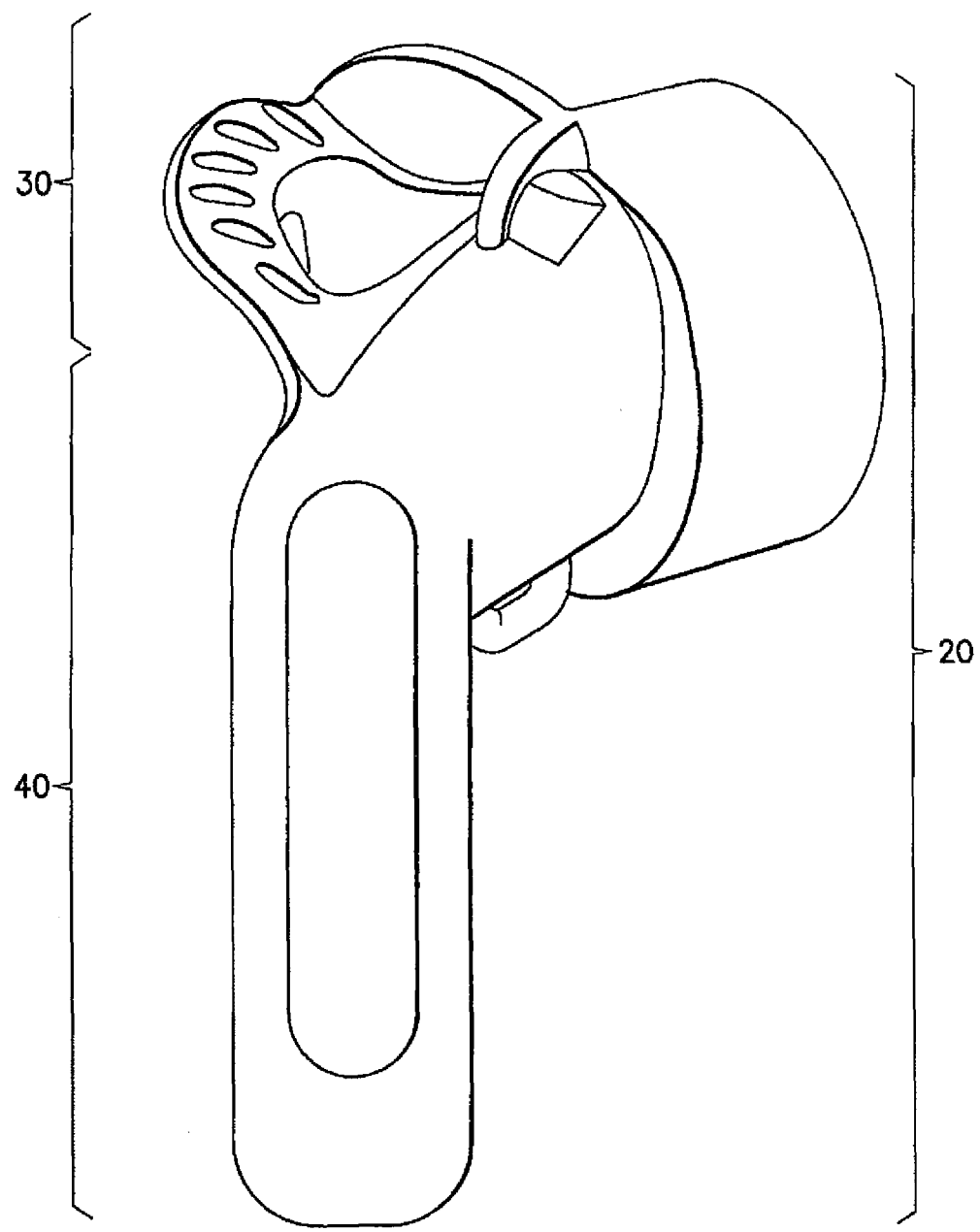

Referring now to FIG. 10, it is seen that this Fig. shows another embodiment of the prosthesis of the present invention. In this embodiment of FIG. 10, some suture holes 66 of the embodiment of FIGS. 4-7 are replaced by a bone-grafting window 72 (such window 72 could, for example, increase the fusion between the greater tuberosity 12 and the lesser tuberosity 13).

Figure 11A:
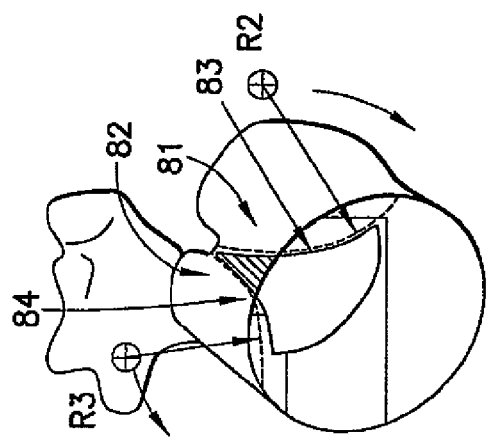
FIGS. 11a and 11b compare an embodiment of the present invention (FIG. 11a) with a conventional design (FIG. 11b) and show certain advantages of the present invention with regard to securing the tuberosities.
Figure 11B:
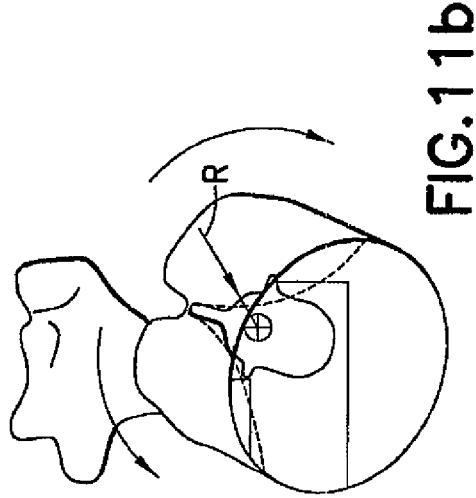

Further, FIGS. 11*a* and 11*b* show certain advantages provided by the unique shape of the metaphyseal portion 60 of the present invention. More particularly, FIG. 11*a* represents an upper view of an embodiment of the present invention in place in the body. The greater tuberosity 12 and the lesser tuberosity 13 are in place around the metaphyseal portion 60. The outer part 63 of the metaphyseal portion 60 provides two anatomical beds 81 and 82 to relocate the tuberosities 12 and 13. As seen in this FIG. 11*a*, these beds 81 and 82 are limited by the anterior-lateral rib and the medial stop provided by the edge 69. Since, in this embodiment, the anterior-lateral rib 64 is anteriorly eccentered by the offset d3 from the frontal plane $\lambda$, the posterior bed 81 is provided a volume higher than that of the anterior bed 82 (i.e., this embodiment of the present invention provides a relatively larger posterior bed 81 to reinsert the greater tuberosity 12 and a relatively smaller anterior bed 82 to reinsert the lesser tuberosity 13). In general, the metaphyseal portion would be symmetric in relation to the frontal plane $\lambda$ only if d3 equal 0 mm, d5 equal 0 mm and $\sigma$ equal 0 degree; for all the other values of d3, d5 and $\sigma$, the metaphyseal portion could be defined as being asymmetric.

Still referring to FIG. 11*a*, a cross section of the metaphyseal portion 60 shows that the edges 83 and 84 of each bed 81 and 82 could be approximated by a radius of curvature R2 and R3 (under this embodiment of the present invention each radius of curvature R2 and R3 may be independent of the other—if desired, R2 and R3 may be dependent upon one another).

Referring now also to FIG. 11*b* (i.e., the Fig. showing the conventional design), it is seen that in comparison to the conventional design, the outer part 63 of this embodiment of the present invention (i.e., the thin, tapered part) may allow the surgeon to preserve the maximum amount of the patient's cancellous bone (indeed, with a conventional design, the surgeon must typically remove some cancellous bone to create the print of the metaphyseal portion in the tuberosities).

Still referring to FIGS. 11*a* and 11*b*, it is seen that the greater tuberosity 12 and the lesser tuberosity 13 are well secured by the present invention. This characteristic is provided by the unique concave curvature of the beds 81 and 82 of this embodiment of the present invention (the concave shape of the beds 81 and 82 creates a natural stability for the tuberosities 12 and 13). In comparison, the curvature of a conventional prosthesis is convex.

Further, in one example (which example is intended to be illustrative and not restrictive), the radius of curvature R2 and/or R3 may be higher than the radius of curvature R4 provided by a conventional design. In this regard, concerning the biomechanical point of view, the moment of force required to initiate the sliding between two components is typically a function of the radius of curvature. As a result, a higher moment of force may be necessary to initiate the sliding of the tuberosities 12 and 13 around the metaphyseal portion 60 of the present invention.

Figure 19:
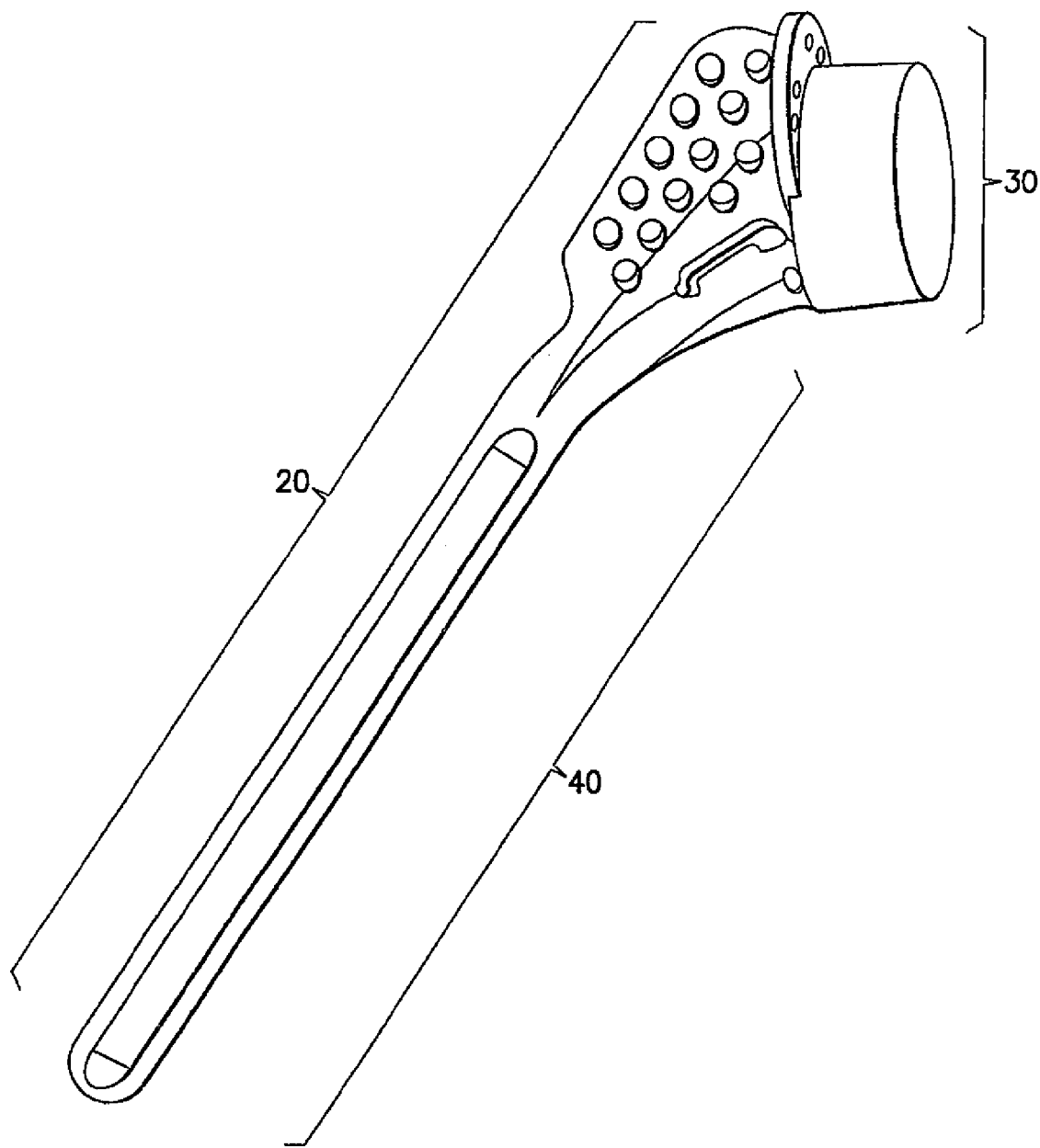
Figure 20:
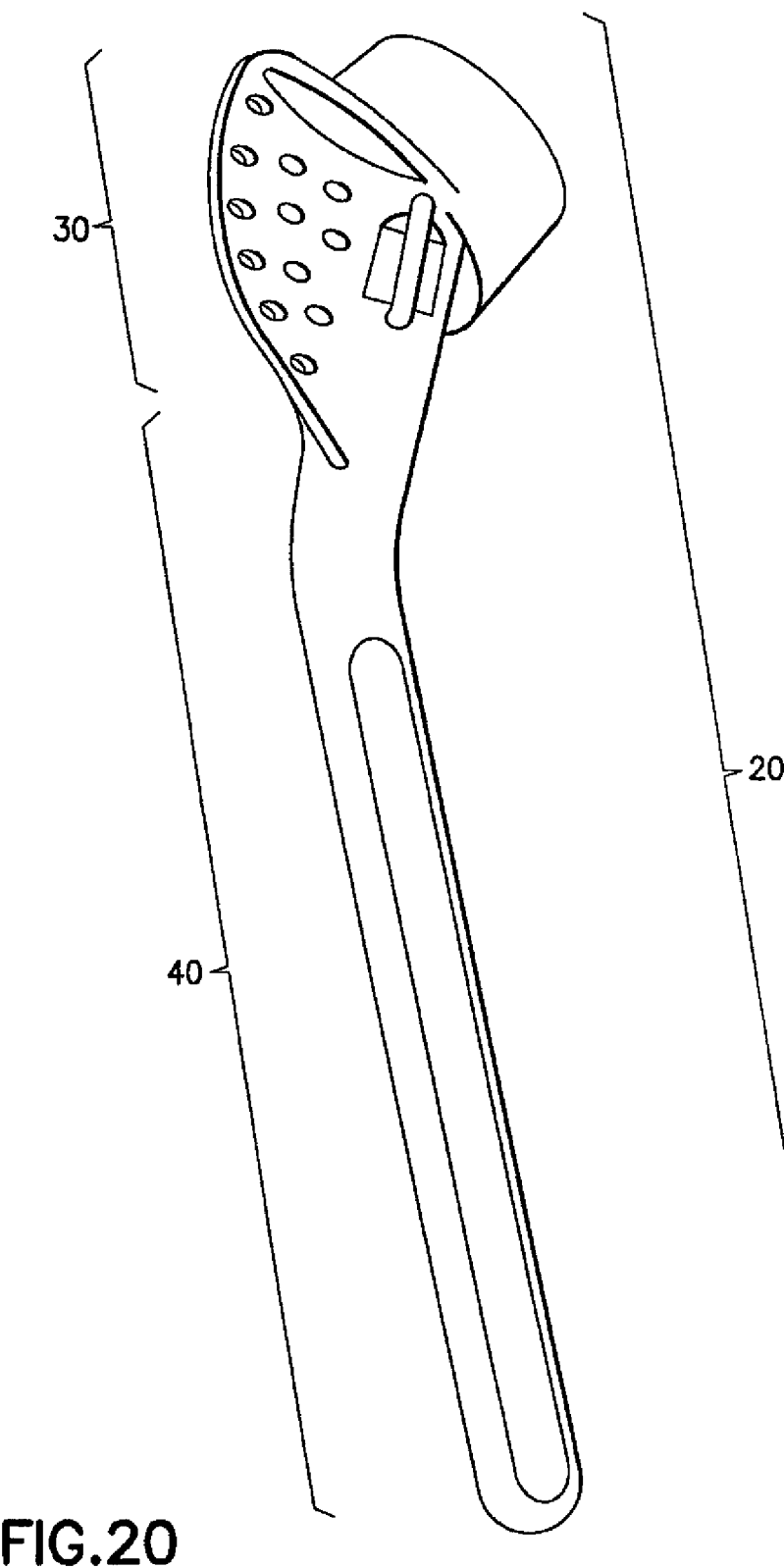
Figure 21:
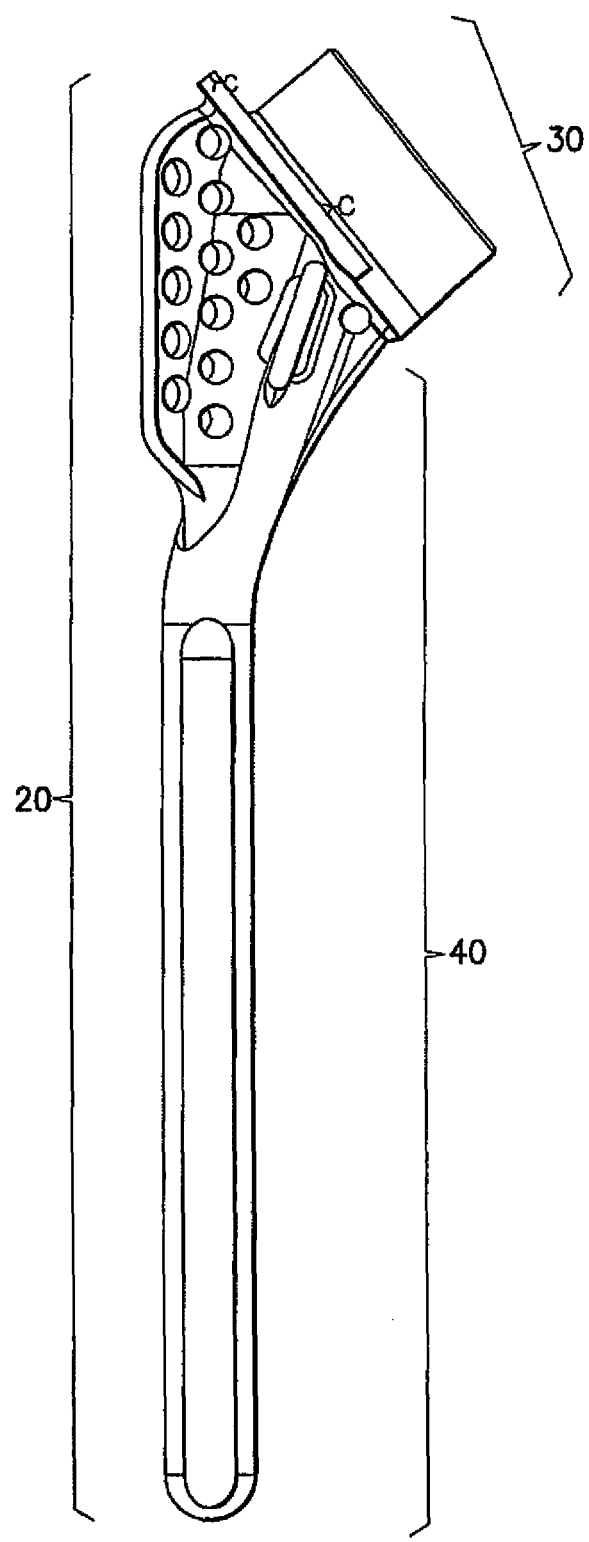

Referring now to FIGS. 12-21, additional views of various embodiments of a humeral prosthesis according to the present invention are shown. Of note, FIGS. 12-18 show a prosthesis including a "window" feature and FIGS. 19-21 show a prosthesis with an array of holes feature. Of further note, these FIGS. 12-21 show, in general, a humeral prosthesis 20 comprising a prosthetic humeral head 30 and a humeral stem 40 (these elements 20, 30 and 40 generally correspond to the same elements shown in FIGS. 4-10 and 11*a*, with the distinctions relating principally to the specific geometry/topography of the different embodiments).

Referring now to FIGS. 22-25, an additional discussion of positioning of the prosthesis of the present invention relative to the patient's bone will be provided. More particularly, it is noted that the inventors have determined that from an anatomical point of view the bicipital groove lateral offset (see, e.g., dimension d6 of FIG. 2) is typically the shortest distance between the intramedullary axis of the proximal humerus and the center of the bicipital groove measured on the medio-lateral plane. This dimension typically varies along the bicipital groove course from proximal to distal. As a direct result, the bicipital groove is typically shaped like a "C" in the medio-lateral plane. The inventors have determined that the maximum lateral offset of the lateral groove is typically obtained around the level of the intersection between the intramedullary axis of the proximal humerus (see, e.g., axis $\gamma$ of FIG. 3) and the projection of the humeral head along the line perpendicular to the anatomical neck (see, e.g., axis $\pi$ of FIGS. 22 and 23). In other words, the most lateral point of the bicipital groove in the medio-lateral plane is typically in direct relation with the center of the referential used (i.e. projection of the humeral head center to the intramedullary axis along the line perpendicular to the anatomical neck).

Thus, based upon the findings of the inventors' anatomical study of the proximal humerus (e.g., concerning the shape of the bicipital groove in the frontal plane), various embodiments of the present invention are presented in which the AL fin of the humeral fracture stem may be C-shaped (of note, this feature may be advantageous for the suture technique and for the stability of the tuberosities). The lateral offset of the AL fin (see, e.g., dimension d7 of FIG. 8) may respect the findings of the anatomical study, since the AL fin of the fracture humeral stem may be C-shaped in the medio-lateral plane. In conformity with the anatomical study, the most lateral point of the AL fin in the medio-lateral plane may be located at the level of the intersection between the intramedullary axis of the humeral stem (see, e.g., axis $\theta$ of FIG. 3) and the projection of the axis of revolution of the morse taper (see, e.g., axis $\Sigma$ of FIG. 6) in the plane $\lambda$.

Figure 22:
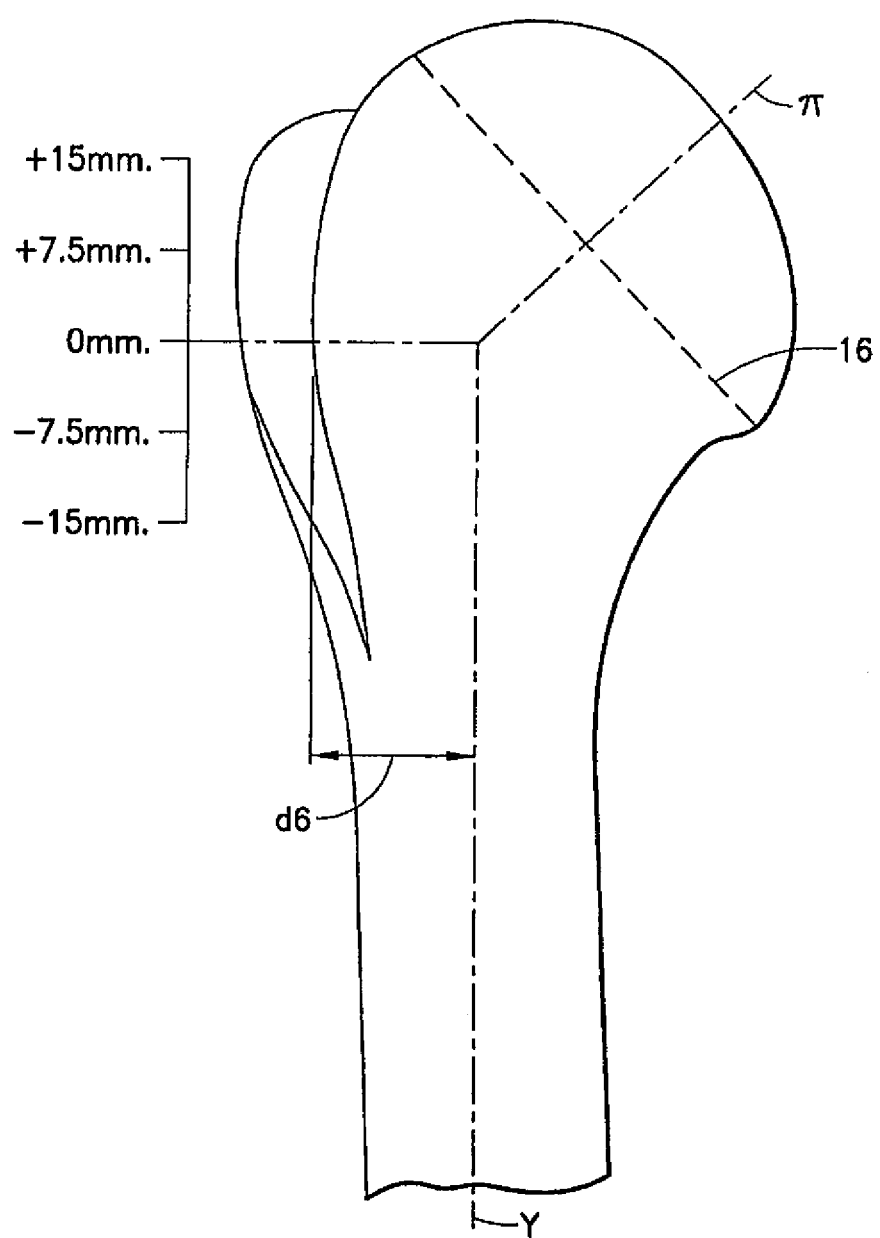
FIGS. 22-25 show various views of bone depicting where a humeral prosthesis according to the present invention may be implanted.
Figure 23:
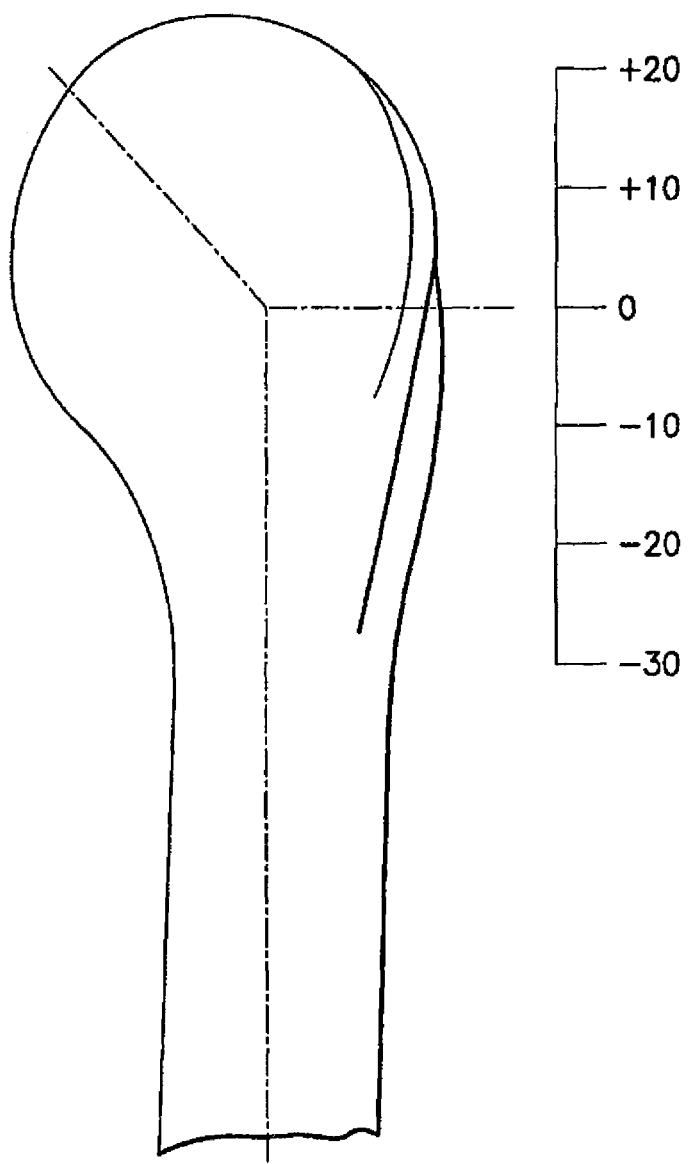

In another example (which example is intended to be illustrative and not restrictive), the prosthesis of the present invention and its relative placement in the body may be defined as follows (see, e.g., FIGS. 2-9). $\omega$ denotes the plane perpendicular to $\beta$ and passing through the intra-medullary axis $\gamma$ of the humeral proximal cylinder 17. The projection of a point of the center of the bicipital groove 14 perpendicularly to the plane $\omega$ is known as the lateral offset of the bicipital groove d6 (in relation to the intra-medullary axis of the proximal humerus $\gamma$). This dimension d6 varies along the bicipital groove 14 course from proximal to distal. To explain this variation, FIGS. 22 and 23 represent thru medio-lateral X-Rays of two dry humeri. A radio-opaque line was pasted along the centerline of each bicipital groove 14 (another definition of the centerline of the bicipital groove is a line linking the deepest points of the bicipital groove along its course from proximal to distal). To associate the lateral offset of the bicipital groove d6 with the location of the projected point of the bicipital groove 14 (point where is measured the lateral offset d6) a referential was created. The vertical distance was used in this referential to qualify the bicipital groove lateral offset. According to the anatomical study performed by the inventors, the largest lateral offset of the bicipital groove is located around the level of the intersection between the intramedullary axis of the proximal humerus $\gamma$ and the projection of the humeral head along the line perpendicular to the anatomical neck $\pi$ (vertical origin of the referential). The maximum lateral offset of the bicipital groove was typically located between +7.5 mm and −7.5 mm in a vertical scale around the intersection between the intramedullary axis of the proximal humerus $\gamma$ and the projection of the humeral head along the line perpendicular to the anatomical neck $\pi$. From this variation of the lateral offset of the bicipital groove d6 along the bicipital groove 14 course, the bicipital groove is shaped as a "C".

In another example (which example is intended to be illustrative and not restrictive), the prosthesis of the present invention and its relative placement in the body may be defined as follows (see, e.g., FIGS. 2-9). $\omega$ denotes the plane perpendicular to A and passing through the intra-medullary axis $\theta$ of the shaft 50 of the humeral stem. The free edge 65 of the anterior-lateral rib 64 may be eccentered from the plane $\psi$ by a distance d7. This dimension d7 varies along the free edge 65 course from proximal to distal. $\Sigma$ is the projection of the axis of revolution of the morse taper 62 in the plane $\lambda$. d8 denotes the vertical distance between the most eccentered point of the free edge 65 and the intersection between the intra-medullary axis $\theta$ of the shaft 50 of the humeral stem and the axis $\Sigma$. In one example (which example is intended to be illustrative and not restrictive), the distance d8 is between −10 mm and +10 mm. According to one embodiment of the present invention the anterior-lateral rib is not straight (according to a medio-lateral view), but is curved. The distance d6 between the bicipital grove 14 and the plane $\omega$ may be approximately the same as the distance d7 between the anterior-lateral rib 64 and the plane $\psi$. The maximum of each dimension d6 and d7 may be obtained approximately at the same vertical level.

Figure 25:
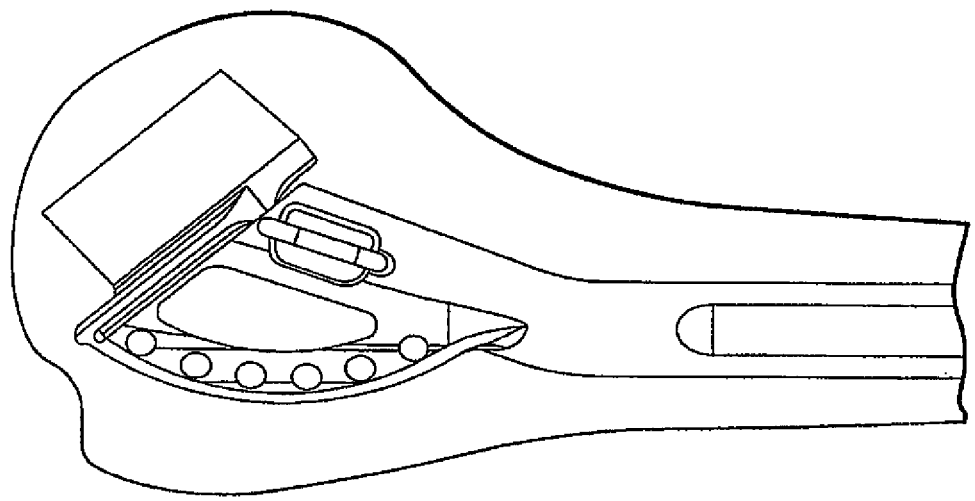
Figure 24:
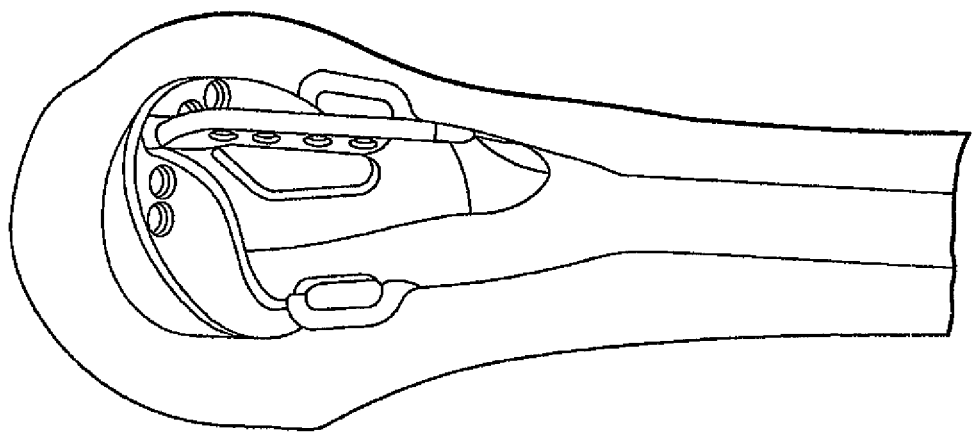

Referring now to FIGS. 24 and 25, one example (which example is intended to be illustrative and not restrictive), of the correspondence between the prosthesis and the anatomy of the proximal humerus is depicted.

Figure 26:
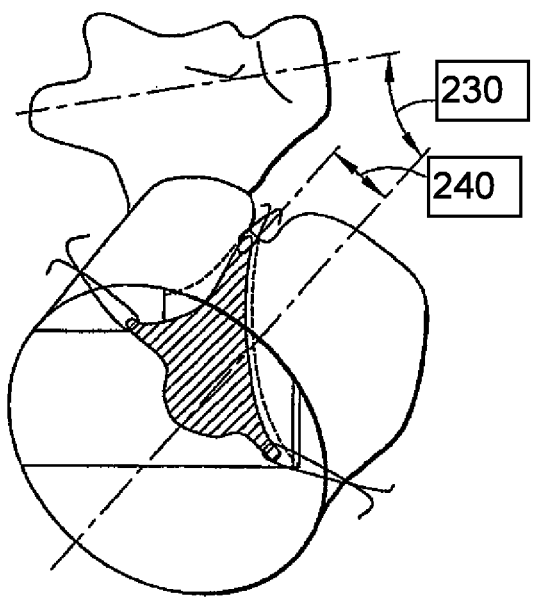
FIGS. 26 and 27 show additional embodiments of a humeral prosthesis according to the present invention.
Figure 27:
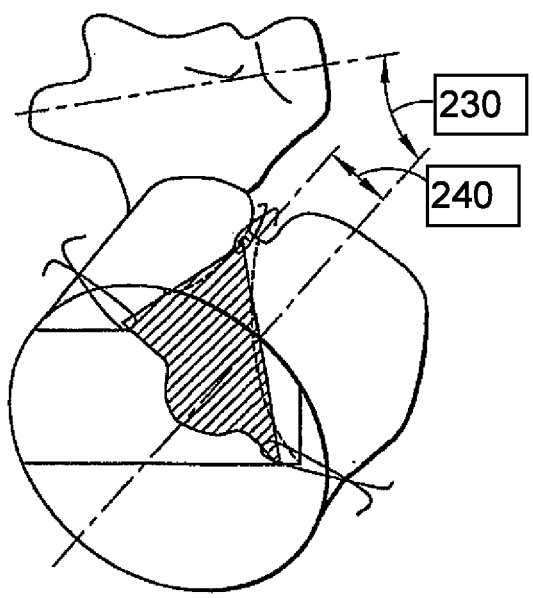

Referring now to FIGS. 26 and 27, two embodiments of a humeral prosthesis according to the present invention are compared. More particularly, FIG. 26 shows that the prosthesis may include two concavities to reinsert the tuberosities while FIG. 27 shows that the prosthesis may have no such concavites. See FIGS. 26 and 27 illustrating the humeral retroversion angle (HRA) 230 and the bicipital groove offset (BCO) 240.

Reference will now be made to one example (which example is intended to be illustrative and not restrictive) of a tuberosity fixation technique according to an embodiment of the present invention (the fixation technique of this example may take advantage of certain original characteristics of the proximal shape of the prosthesis of an embodiment of the present invention). Of note, this example fixation technique will be described in the context of a process carried out on a cadaver.

More particularly, an artificial four-part fracture was created on the right humerus of the cadaver. Using an oscillating saw, the surgeon resected the humeral head at the anatomic neck and separated the tuberosities from the shaft at the surgical neck. The tuberosities were then fractured, with the facture line consistently occurring along the bicipital groove.

The surgeon reamed the medullary canal using an eleven-millimeter reamer and introduced a twelve-millimeter stem into the humerus shaft (slightly press-fit). He oriented the stem to the retroversion by aligning the anterior-lateral fin with the center of the bicipital groove. The surgeon then compared the resected humeral head with the available prosthetic humeral heads. Next, he attached the proper size humeral head to the humeral stem. The surgeon placed the humeral stem at the correct height to allow an anatomic reconstruction of the tuberosities. The number of lateral suture holes in direct relation with the shaft was recorded. Lastly, he performed a provisional reduction of the tuberosities around the prosthesis. It was observed in this process that the anatomical neck was parallel to the bottom face of the humeral head. Afterwards, the surgeon removed the trial prosthesis from the shaft.

Referring now more particularly to the tuberosity fixation, it is noted that the surgeon used a total of six Ethibond #2 mattress sutures for tuberosity fixation—three for the greater tuberosity (two horizontal sutures and one vertical) and three for the lesser tuberosity (two horizontal sutures and one vertical).

Figure 28:
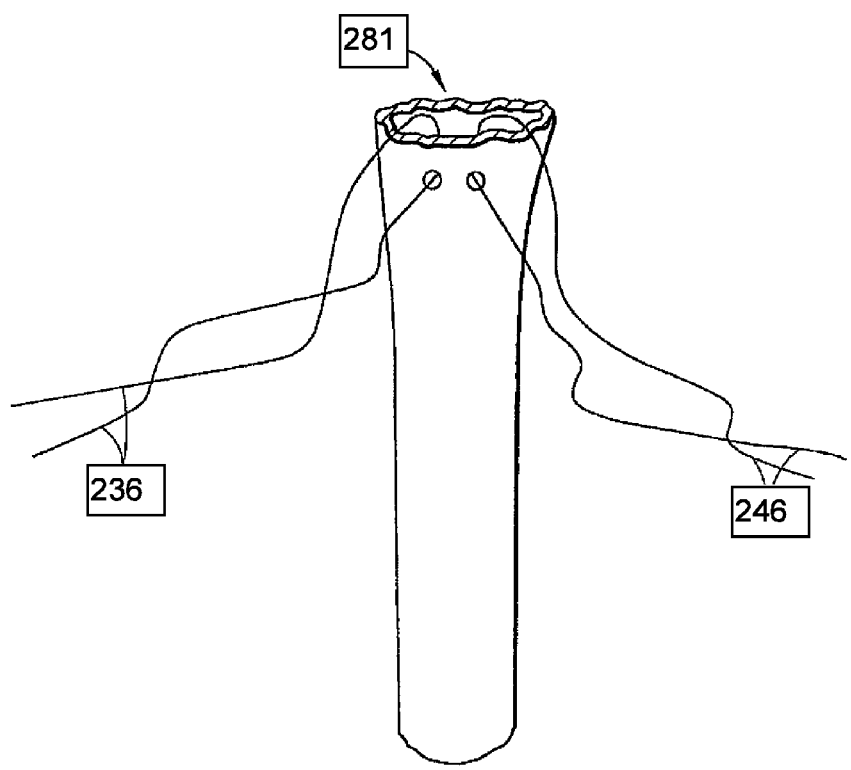
FIGS. 28-36 show additional views associated with how a humeral prosthesis according to the present invention may be implanted.

The surgeon drilled two holes in the proximal humerus shaft—one anterior and one posterior to the bicipital groove 281 (see FIG. 28). Next, he passed a suture through each hole. The lateral suture (First Vertical suture for the Greater Tuberosity, GTV1) 236 was intended to secure the greater tuberosity longitudinally, while the anterior suture (First Vertical suture for the Lesser Tuberosity, LTV1) 246 was intended to secure the lesser tuberosity longitudinally.

The surgeon inserted the humeral stem using hand pressure at the proper height and retroversion, which was previously determined during the trial stage. He passed two horizontal sutures between the greater tuberosity and humeral stem. The surgeon passed the first suture (First Horizontal suture for the Greater Tuberosity, GTH1) 232 through the lower portion of the infraspinatus tendon as it inserted into the greater tuberosity, through the posterior handle 293 (see, e.g., FIGS. 29 and 30) and through an inferior lateral suture hole of the anterior-lateral fin 291 (see, e.g., FIGS. 29 and 30).

Figure 29:
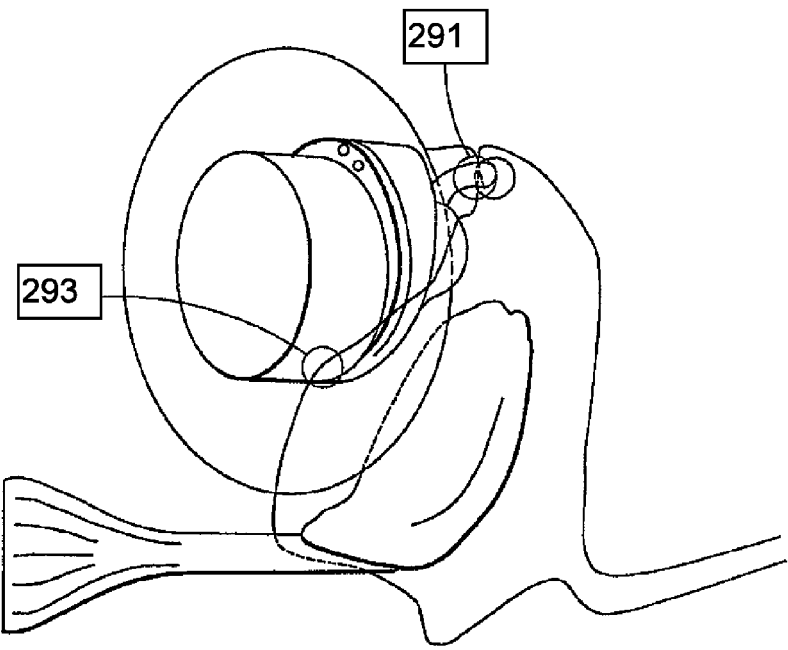
Figure 30:
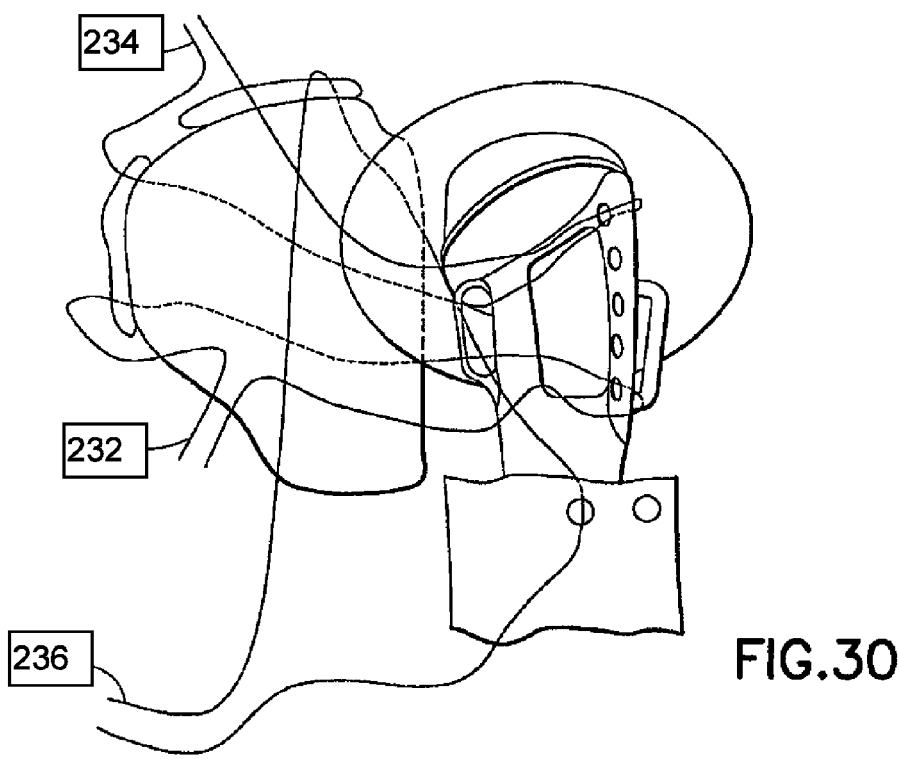

He passed the second suture (Second Horizontal suture for the Greater Tuberosity, GTH2) 234 through the upper portion of the infraspinatus tendon as it inserted into the greater tuberosity, through the posterior handle 293 (see, e.g., FIGS. 29 and 30) and through a superior lateral suture hole of the anterior-lateral fin 291 (see, e.g., FIGS. 29 and 30).

Next, he passed the vertical suture (GTV1) 236 through the supraspinatus tendon as it inserted into the greater tuberosity (see FIGS. 29 and 30).

The surgeon passed two horizontal sutures between the lesser tuberosity and the humeral stem. He passed the first suture (First Horizontal suture for the Lesser tuberosity LTH1) 242 through the lower portion of the subscapularis tendon as it inserted into the lesser tuberosity, through the anterior handle 295 (see, e.g., FIGS. 31 and 32) and through an inferior lateral suture hole of the anterior-lateral fin 291 (see, e.g., FIGS. 31 and 32).

Next, he passed the second suture (Second Horizontal suture for the Lesser tuberosity LTH2) 244 through the upper portion of the subscapularis tendon as it inserted into the lesser tuberosity, through the anterior handle 295 and through a superior lateral suture hole of the anterior-lateral fin 291.

Figure 31:
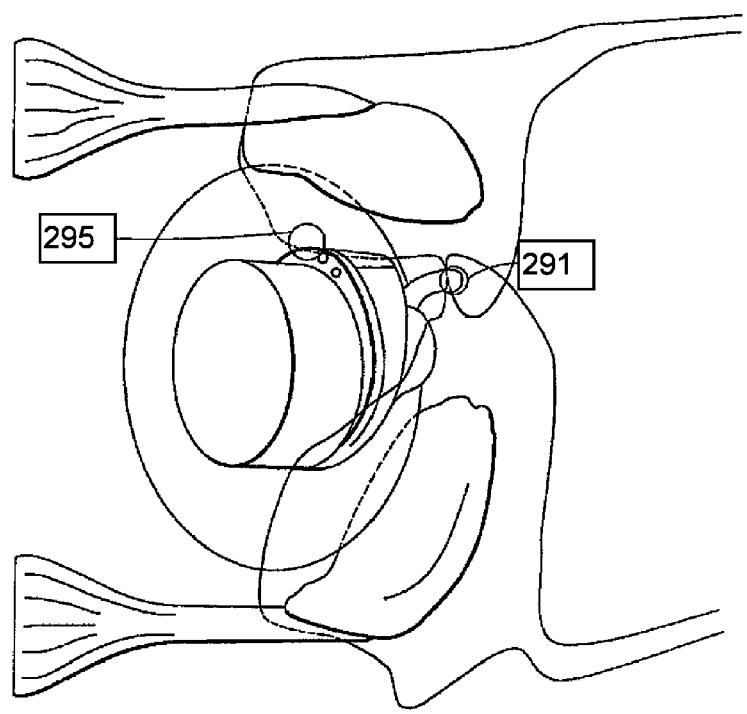
Figure 32:
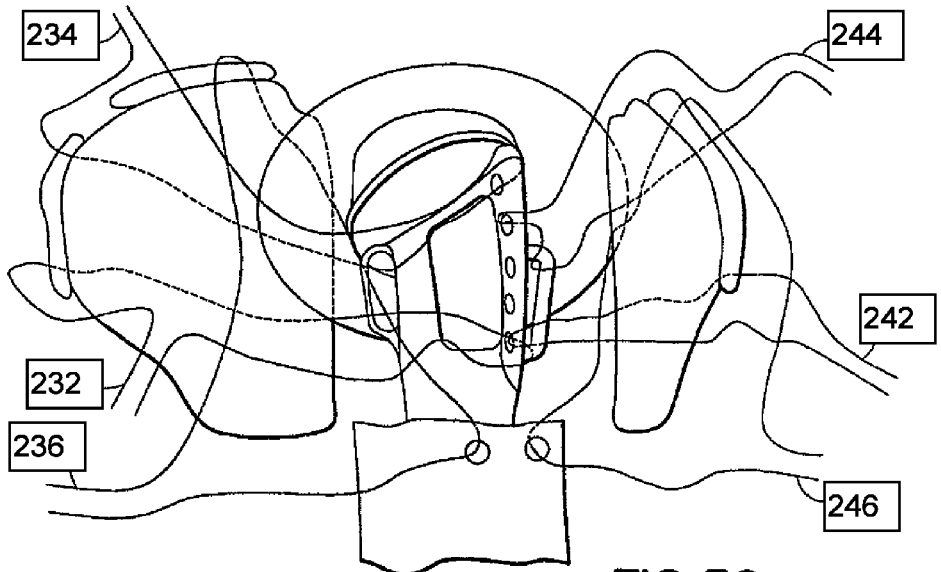

He then passed the vertical suture (LTV1) 246 through the top upper portion of the subscapularis tendon near the rotator interval as it inserted into the lesser tuberosity (see FIGS. 31 and 32).

Figure 33:
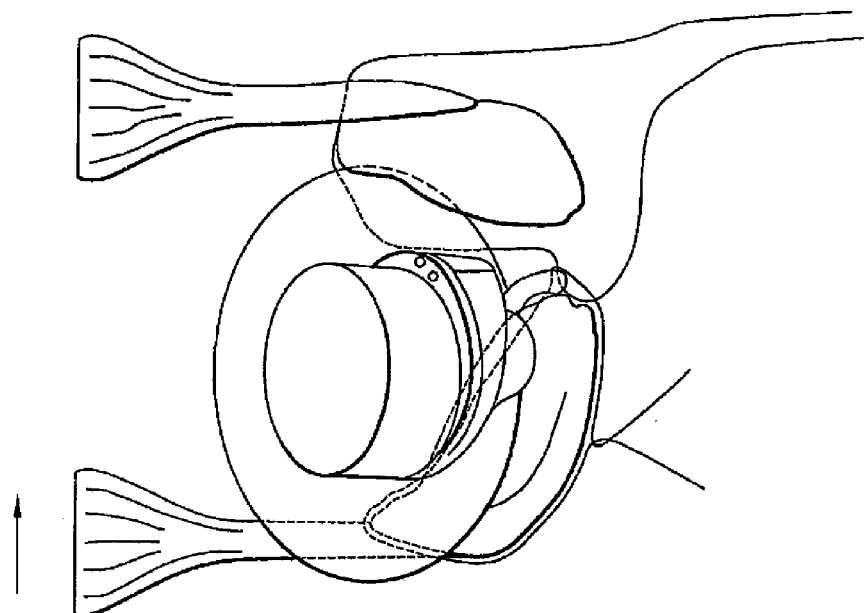
Figure 34:
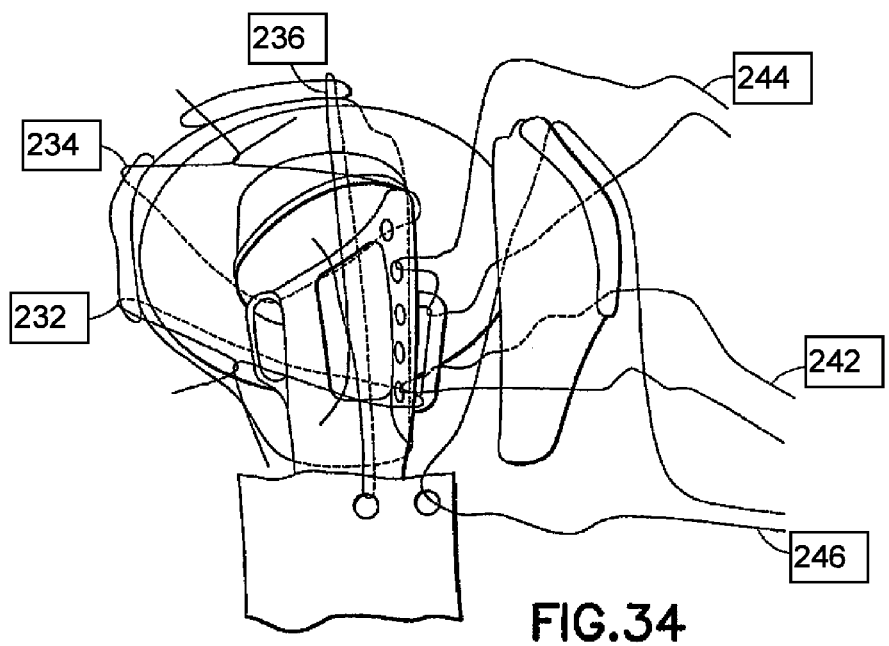

He then tied the sutures for the greater tuberosity. To do this, he slightly rotated the arm externally (see FIGS. 33 and 34).

Figure 35:
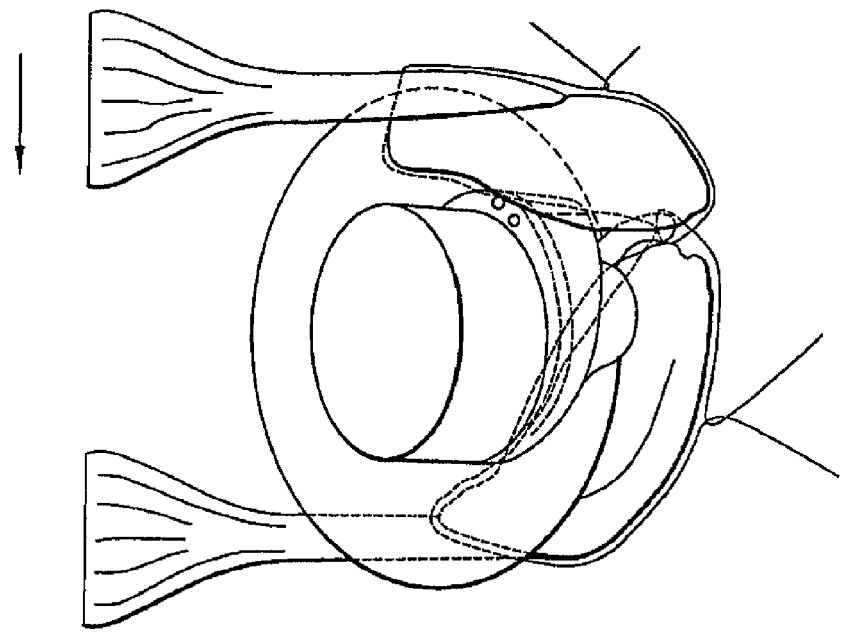
Figure 36:
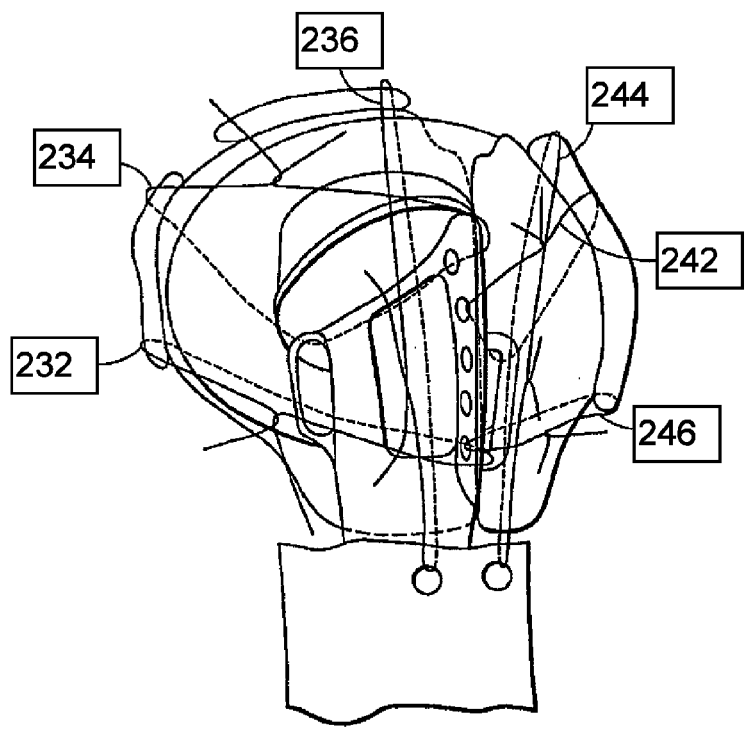

Finally, the sutures for the lesser tuberosity were tied. For this, the arm was in neutral rotation (see FIGS. 35 and 36).

In another embodiment of the present invention a prosthesis may be modular, with different head diameters (e.g., from 38 to 53 mm) and stems in different sizes (e.g., diameter, 7 to 12 mm; length, 135 mm). The metaphyseal portion of the stem may be characterized by the presence of two cavities, one posterior and one anterior, intended to receive the lesser and greater tuberosities. The shape of each cavity may help to stabilize (e.g., initially and/or long term) each tuberosity.

In another embodiment of the present invention a prosthesis may be provided which: (a) reduces or eliminates improper prosthesis placement with regard to the humeral head length and retroversion (regarding the retroversion, alignment of the anterior-lateral fin with the distal portion of the bicipital groove may help ensure correct prosthesis positioning in orientation in fracture situations); (b) reduces or eliminates incorrect location of the tuberosities in the frontal plane, transverse plane or both; and/or (c) reduces or eliminates poor tuberosity fixation (preventing tuberosity malposition and migration may be critical for successful fracture shoulder replacement).

In other embodiments of the present invention one or more of the following features may be provided: (a) independent adjustability of anatomic parameters (e.g., four anatomic parameters may be adjustable in situ); (b) precise anatomical replication with a simple surgical technique (e.g., precise anatomical replication with a cut and cover technique); (c) an innovative glenoid (e.g., combine essentially any head size with essentially any glenoid size while still optimizing radial mismatch; (d) robust scope (e.g., offer intra-operative flexibility to the surgeon); (e) offset anterior-lateral fin (e.g. for alignment to distal bicipital groove) and asymmetric tuberosity beds (e.g., defining the next generation in four-part fracture reconstruction); (f) grafting window (e.g., for promoting tuberosity reunion through the anterior-lateral fin (bone graft may be used to initiate reunion)); (g) a device and method which allow the surgeon to recreate the patient anatomy; (h) a device and method which allow the correct relocation of the tuberosities (e.g., length and retroversion); (i) a device and method which allow the stabilization and long term fixation of the tuberosities; (j) a device and method which allow the preservation (as much as possible) of patient bone (e.g., cancellous bone); (k) a device and method which respect the anatomical fracture lines and avoid tuberosities lateralization (e.g., respects the rotator cuff tensile).

In another embodiment a shoulder prosthesis for implantation in a patient is provided, comprising: a shaft portion for attachment to a humerus shaft of the patient, which shaft portion includes a proximal end and a distal end; a metaphyseal portion, which metaphyseal portion includes a body, a proximal end and a distal end; a cavity defining element including first and second opposed curved surfaces, which cavity defining element extends from the body of the metaphyseal portion; and a flange portion; wherein the distal end of the metaphyseal portion abuts the proximal end of the shaft portion and the proximal end of the metaphyseal portion abuts the flange portion; wherein the metaphyseal portion includes a first concavity having a concave curved surface for receiving at least a part of a greater tuberosity of the patient and a second concavity having a concave curved surface for receiving at least a part of a lesser tuberosity of the patient; wherein the first concavity is defined at least in part by at least a portion of the first opposed curved surface of the cavity defining element extending from the body of the metaphyseal portion; and wherein the second concavity is defined at least in part by at least a portion of the second opposed curved surface of the cavity defining element extending from the body of the metaphyseal portion.

In one example (which example is intended to be illustrative and not restrictive), the cavity defining element may extend in a generally anterial-lateral orientation.

In another example (which example is intended to be illustrative and not restrictive), the first concavity and the second concavity may be asymmetric.

In another example (which example is intended to be illustrative and not restrictive), the first concavity and the second concavity may have different volumes.

In another example (which example is intended to be illustrative and not restrictive), a thickness of the cavity defining element may decrease as a function of distance from the body of the metaphyseal portion.

In another example (which example is intended to be illustrative and not restrictive), the first concavity may be configured to receive essentially the entire greater tuberosity and the second concavity may be configured to receive essentially the entire lesser tuberosity.

In another example (which example is intended to be illustrative and not restrictive), the first concavity may be configured to receive essentially the entire greater tuberosity without removal of substantial bone mass therefrom and the second concavity may be configured to receive essentially the entire lesser tuberosity without removal of substantial bone mass therefrom.

In another example (which example is intended to be illustrative and not restrictive), the first concavity may be configured to receive essentially the entire greater tuberosity without substantially changing the shape thereof and the second concavity may be configured to receive essentially the entire lesser tuberosity without substantially changing the shape thereof.

In another example (which example is intended to be illustrative and not restrictive), the first concavity may have an elongated shape and the second concavity may have an elongated shape.

In another example (which example is intended to be illustrative and not restrictive), the shoulder prosthesis may further comprise a prosthetic humeral head.

In another example (which example is intended to be illustrative and not restrictive), the prosthetic humeral head may be attached to the flange portion.

In another example (which example is intended to be illustrative and not restrictive), the prosthetic humeral head may be attached to the flange portion via a Morse Taper.

In another example (which example is intended to be illustrative and not restrictive), the Morse Taper may be offset from center in a posterior direction.

In another example (which example is intended to be illustrative and not restrictive), the flange may include at least one hole for receiving a suture.

In another example (which example is intended to be illustrative and not restrictive), the shaft portion may be adapted to be anchored in a medullary canal of the humerus shaft.

In another example (which example is intended to be illustrative and not restrictive), the shaft portion may include at least one groove for gripping the medullary canal of the humerus shaft.

In another example (which example is intended to be illustrative and not restrictive), the cavity defining element may have at least one aperture therethrough between the two opposed curved surfaces.

In another example (which example is intended to be illustrative and not restrictive), the aperture may be selected from the group including, but not limited to: (a) a suture hole for receiving a suture; and (b) a window through which osseous fusion may occur.

In another embodiment a shoulder prosthesis for implantation in a patient is provided, comprising: a shaft portion for attachment to a humerus shaft of the patient, which shaft portion includes a proximal end and a distal end; a metaphyseal portion, which metaphyseal portion includes a body, a proximal end and a distal end; a cavity defining element extending from the body of the metaphyseal portion, which cavity defining element includes a first curved surface and a second curved surface; and a flange portion; wherein the distal end of the metaphyseal portion abuts the proximal end of the shaft portion and the proximal end of the metaphyseal portion abuts the flange portion; wherein the metaphyseal portion includes a first concavity having a concave curved surface for receiving at least a part of a greater tuberosity of the patient; wherein the metaphyseal portion includes a second concavity having a concave curved surface for receiving at least a part of a lesser tuberosity of the patient; wherein the first concavity is defined at least in part by the abutting combination of the first curved surface of the cavity defining element extending from the body of the metaphyseal portion and a first curved surface of the body of the metaphyseal portion; and wherein the second concavity is defined at least in part by the abutting combination of the second curved surface of the cavity defining element extending from the body of the metaphyseal portion and a second curved surface of the body of the metaphyseal portion.

In one example (which example is intended to be illustrative and not restrictive), the cavity defining element may extend in a generally anterial-lateral orientation.

In another example (which example is intended to be illustrative and not restrictive), the first concavity and the second concavity may be asymmetric.

In another example (which example is intended to be illustrative and not restrictive), the first concavity and the second concavity may have different volumes.

In another example (which example is intended to be illustrative and not restrictive), a thickness of the cavity defining element may decrease as a function of distance from the body of the metaphyseal portion.

In another example (which example is intended to be illustrative and not restrictive), the first concavity may be configured to receive essentially the entire greater tuberosity and the second concavity may be configured to receive essentially the entire lesser tuberosity.

In another example (which example is intended to be illustrative and not restrictive), the first concavity may be configured to receive essentially the entire greater tuberosity without removal of substantial bone mass therefrom and the second concavity may be configured to receive essentially the entire lesser tuberosity without removal of substantial bone mass therefrom.

In another example (which example is intended to be illustrative and not restrictive), the first concavity may be configured to receive essentially the entire greater tuberosity without substantially changing the shape thereof and the second concavity may be configured to receive essentially the entire lesser tuberosity without substantially changing the shape thereof.

In another example (which example is intended to be illustrative and not restrictive), the first concavity may have an elongated shape and the second concavity may have an elongated shape.

In another example (which example is intended to be illustrative and not restrictive), the shoulder prosthesis may further comprise a prosthetic humeral head.

In another example (which example is intended to be illustrative and not restrictive), the prosthetic humeral head may be attached to the flange portion.

In another example (which example is intended to be illustrative and not restrictive), the prosthetic humeral head may be attached to the flange portion via a Morse Taper.

In another example (which example is intended to be illustrative and not restrictive), the Morse Taper may be offset from center in a posterior direction.

In another example (which example is intended to be illustrative and not restrictive), the flange may include at least one hole for receiving a suture.

In another example (which example is intended to be illustrative and not restrictive), the shaft portion may be adapted to be anchored in a medullary canal of the humerus shaft.

In another example (which example is intended to be illustrative and not restrictive), the shaft portion may include at least one groove for gripping the medullary canal of the humerus shaft.

In another example (which example is intended to be illustrative and not restrictive), the cavity defining element may have at least one aperture therethrough.

In another example (which example is intended to be illustrative and not restrictive), the aperture may be selected from the group including, but not limited to: (a) a suture hole for receiving a suture; and (b) a window through which osseous fusion may occur.

In another embodiment a shoulder prosthesis for implantation in a patient is provided, comprising: a shaft portion for attachment to a humerus shaft of the patient, which shaft portion includes a proximal end and a distal end; a metaphyseal portion, which metaphyseal portion includes a body, a proximal end and a distal end; a cavity defining element extending from the body of the metaphyseal portion, which cavity defining element includes a curved surface; wherein the distal end of the metaphyseal portion abuts the proximal end of the shaft portion and the proximal end of the metaphyseal portion abuts the flange portion; wherein the metaphyseal portion includes a concavity having a concave curved surface for receiving at least a part of one of a greater tuberosity of the patient and a lesser tuberosity of the patient; and wherein the concavity is defined at least in part by the abutting combination of a curved surface of the body of the metaphyseal portion and the curved surface of the cavity defining element extending from the body of the metaphyseal portion.

In another embodiment a shoulder prosthesis for implantation in a patient is provided, comprising: a shaft portion for attachment to a humerus shaft of the patient, which shaft portion includes a proximal end and a distal end; a metaphyseal portion, which metaphyseal portion includes a body, a proximal end and a distal end; a fin; and a flange portion; wherein the distal end of the metaphyseal portion abuts the proximal end of the shaft portion and the proximal end of the metaphyseal portion abuts the flange portion; wherein the fin extends from the metaphyseal portion in a generally anterior-lateral direction; wherein a free edge of the fin is offset in an anterior direction from a frontal plane of the prosthesis; and wherein the free edge of the fin substantially mimics at least a portion of an anatomical location of a bicipital groove.

In one example (which example is intended to be illustrative and not restrictive), the free edge of the fin may substantially mimic essentially the entire anatomical location of the bicipital groove.

In another example (which example is intended to be illustrative and not restrictive), the free edge of the fin may substantially mimic essentially the entire anatomical location of the bicipital groove along a centerline of the bicipital groove.

In another example (which example is intended to be illustrative and not restrictive), an offset distance of a point on the free edge of the fin from a sagital plane of the prosthesis may vary with the vertical location of the point on the free edge of the fin.

In another example (which example is intended to be illustrative and not restrictive), a thickness of the fin may decrease as a function of distance from the body of the metaphyseal portion.

In another example (which example is intended to be illustrative and not restrictive), the fin may define a first tuberosity receiving portion configured to receive essentially the entire greater tuberosity and a second tuberosity receiving portion configured to receive essentially the entire lesser tuberosity.

In another example (which example is intended to be illustrative and not restrictive), the first tuberosity receiving portion may be configured to receive essentially the entire greater tuberosity without removal of substantial bone mass therefrom and the second tuberosity receiving portion may be configured to receive essentially the entire lesser tuberosity without removal of substantial bone mass therefrom.

In another example (which example is intended to be illustrative and not restrictive), the first tuberosity receiving portion may be configured to receive essentially the entire greater tuberosity without substantially changing the shape thereof and the second tuberosity receiving portion may be configured to receive essentially the entire lesser tuberosity without substantially changing the shape thereof.

In another example (which example is intended to be illustrative and not restrictive), the first tuberosity receiving portion may have an elongated shape and the second tuberosity receiving portion may have an elongated shape.

In another example (which example is intended to be illustrative and not restrictive), the shoulder prosthesis may further comprise a prosthetic humeral head.

In another example (which example is intended to be illustrative and not restrictive), the prosthetic humeral head may be attached to the flange portion.

In another example (which example is intended to be illustrative and not restrictive), the prosthetic humeral head may be attached to the flange portion via a Morse Taper.

In another example (which example is intended to be illustrative and not restrictive), the Morse Taper may be offset from center in a posterior direction.

In another example (which example is intended to be illustrative and not restrictive), the flange may include at least one hole for receiving a suture.

In another example (which example is intended to be illustrative and not restrictive), the shaft portion may be adapted to be anchored in a medullary canal of the humerus shaft.

In another example (which example is intended to be illustrative and not restrictive), the shaft portion may include at least one groove for gripping the medullary canal of the humerus shaft.

In another example (which example is intended to be illustrative and not restrictive), the fin may have at least one aperture therethrough.

In another example (which example is intended to be illustrative and not restrictive), the aperture may be selected from the group including, but not limited to: (a) a suture hole for receiving a suture; and (b) a window through which osseous fusion may occur.

In another embodiment a shoulder prosthesis for implantation in a patient is provided, comprising: a shaft portion for attachment to a humerus shaft of the patient, which shaft portion includes a proximal end and a distal end; a metaphyseal portion, which metaphyseal portion includes a body, a proximal end and a distal end; a fin; and a flange portion; wherein the distal end of the metaphyseal portion abuts the proximal end of the shaft portion and the proximal end of the metaphyseal portion abuts the flange portion; and wherein a free edge of the fin substantially mimics at least a portion of a three-dimensional anatomical location of a bicipital groove.

In one example (which example is intended to be illustrative and not restrictive), the free edge of the fin may substantially mimic essentially the entire three-dimensional anatomical location of the bicipital groove.

In another example (which example is intended to be illustrative and not restrictive), the free edge of the fin may substantially mimic essentially the entire three-dimensional anatomical location of the bicipital groove along a centerline of the bicipital groove.

In another example (which example is intended to be illustrative and not restrictive), an offset distance of a point on the free edge of the fin from a centerline of the shaft portion may vary with the vertical location of the point on the free edge of the fin.

In another example (which example is intended to be illustrative and not restrictive), a thickness of the fin may decrease as a function of distance from the body of the metaphyseal portion.

In another example (which example is intended to be illustrative and not restrictive), the fin may define a first tuberosity receiving portion configured to receive essentially the entire greater tuberosity and a second tuberosity receiving portion configured to receive essentially the entire lesser tuberosity.

In another example (which example is intended to be illustrative and not restrictive), the first tuberosity receiving portion may be configured to receive essentially the entire greater tuberosity without removal of substantial bone mass therefrom and the second tuberosity receiving portion may be configured to receive essentially the entire lesser tuberosity without removal of substantial bone mass therefrom.

In another example (which example is intended to be illustrative and not restrictive), the first tuberosity receiving portion may be configured to receive essentially the entire greater tuberosity without substantially changing the shape thereof and the second tuberosity receiving portion may be configured to receive essentially the entire lesser tuberosity without substantially changing the shape thereof.

In another example (which example is intended to be illustrative and not restrictive), the first tuberosity receiving portion may have an elongated shape and the second tuberosity receiving portion may have an elongated shape.

In another example (which example is intended to be illustrative and not restrictive), the shoulder prosthesis may further comprise a prosthetic humeral head.

In another example (which example is intended to be illustrative and not restrictive), the prosthetic humeral head may be attached to the flange portion.

In another example (which example is intended to be illustrative and not restrictive), the prosthetic humeral head may be attached to the flange portion via a Morse Taper.

In another example (which example is intended to be illustrative and not restrictive), the Morse Taper may be offset from center in a posterior direction.

In another example (which example is intended to be illustrative and not restrictive), the flange may include at least one hole for receiving a suture.

In another example (which example is intended to be illustrative and not restrictive), the shaft portion may be adapted to be anchored in a medullary canal of the humerus shaft.

In another example (which example is intended to be illustrative and not restrictive), the shaft portion may include at least one groove for gripping the medullary canal of the humerus shaft.

In another example (which example is intended to be illustrative and not restrictive), the fin may have at least one aperture therethrough.

In another example (which example is intended to be illustrative and not restrictive), the aperture may be selected from the group including, but not limited to: (a) a suture hole for receiving a suture; and (b) a window through which osseous fusion may occur.

Finally, it is noted that the term "plane" is intended to refer to a geometric construct utilized for defining a structure in 3-dimensional space (and not necessarily to an actual physical surface or object).

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive. Further, any desired number and shape of hole(s), window(s), shaft groove(s), etc. may be utilized (and may be placed in any desired location(s) on the prosthesis). Further still, while the term "rib" has been used throughout this application and may be thought to imply a separate, stand-alone feature, it is to be understood that the invention may, of course, utilize one or more surfaces of an essentially continuous structure in addition to (or in place of) a "rib". Further still, any steps relating to uses and/or applications of the prosthesis may be performed in any desired order.

What is claimed is:

1. A shoulder prosthesis for implantation in a patient, comprising:
    a shaft portion for attachment to a humerus shaft of the patient, wherein the shaft portion includes a proximal end and a distal end;
    a metaphyseal portion, wherein the metaphyseal portion includes a body, a proximal end and a distal end;
    a fin including first and second opposed surfaces, wherein the fin extends from the body of the metaphyseal portion; and
    a flange portion;
    wherein the distal end of the metaphyseal portion abuts the proximal end of the shaft portion and the proximal end of the metaphyseal portion abuts the flange portion;
    wherein the metaphyseal portion includes a first concavity having a surface for receiving at least a part of a greater tuberosity of the patient and a second concavity having a surface for receiving at least a part of a lesser tuberosity of the patient;
    wherein the first concavity is defined at least in part by at least a portion of the first opposed surface of the fin element extending from the body of the metaphyseal portion;
    wherein the second concavity is defined at least in part by at least a portion of the second opposed surface of the fin element extending from the body of the metaphyseal portion;
    wherein the first concavity and the second concavity are asymmetric;
    wherein the fin extends from the body of the metaphyseal portion in a generally anterior-lateral direction;
    wherein a free edge of the fin is offset in an anterior direction from a frontal plane of the prosthesis; and
    wherein a position of the free edge of the fin substantially mimics a position of essentially an entire anatomical location of a bicipital groove.

2. The shoulder prosthesis of claim 1, wherein the position of the free edge of the fin substantially mimics the position of essentially the entire anatomical location of the bicipital groove along a centerline of the bicipital groove.

3. The shoulder prosthesis of claim 2, wherein an offset distance of a point on the free edge of the fin from a sagital plane of the prosthesis varies with the vertical location of the point on the free edge of the fin.

4. The shoulder prosthesis of claim 1, wherein a thickness of the fin decreases as a function of distance from the body of the metaphyseal portion.

5. The shoulder prosthesis of claim 1, wherein the fin defines a first tuberosity receiving portion configured to receive essentially the entire greater tuberosity and a second tuberosity receiving portion configured to receive essentially the entire lesser tuberosity.

6. The shoulder prosthesis of claim 5, wherein the first tuberosity receiving portion is configured to receive essentially the entire greater tuberosity without removal of substantial bone mass therefrom and the second tuberosity receiving portion is configured to receive essentially the entire lesser tuberosity without removal of substantial bone mass therefrom.

7. The shoulder prosthesis of claim 5, wherein the first tuberosity receiving portion is configured to receive essentially the entire greater tuberosity without substantially changing the shape thereof and the second tuberosity receiving portion is configured to receive essentially the entire lesser tuberosity without substantially changing the shape thereof.

8. The shoulder prosthesis of claim 5, wherein the first tuberosity receiving portion has an elongated shape and the second tuberosity receiving portion has an elongated shape.

9. The shoulder prosthesis of claim 1, further comprising a prosthetic humeral head.

10. The shoulder prosthesis of claim 9, wherein the prosthetic humeral head is attached to the flange portion.

11. The shoulder prosthesis of claim 10, wherein the prosthetic humeral head is attached to the flange portion via a Morse Taper.

12. The shoulder prosthesis of claim 11, wherein the Morse Taper is offset from center in a posterior direction.

13. The shoulder prosthesis of claim 1, wherein the flange includes at least one hole for receiving a suture.

14. The shoulder prosthesis of claim 1, wherein the shaft portion is adapted to be anchored in a medullary canal of the humerus shaft.

15. The shoulder prosthesis of claim 14, wherein the shaft portion includes at least one groove for gripping the medullary canal of the humerus shaft.

16. The shoulder prosthesis of claim 1, wherein the fin has at least one aperture therethrough.

17. The shoulder prosthesis of claim 16, wherein the aperture is selected from the group including: (a) a suture hole for receiving a suture; and (b) a window through which osseous fusion may occur.

18. A shoulder prosthesis for implantation in a patient, comprising:
a shaft portion for attachment to a humerus shaft of the patient, wherein the shaft portion includes a proximal end and a distal end;
a metaphyseal portion, wherein the metaphyseal portion includes a body, a proximal end and a distal end;
a fin including first and second opposed surfaces, wherein the fin extends from the body of the metaphyseal portion; and
a flange portion;
wherein the distal end of the metaphyseal portion abuts the proximal end of the shaft portion and the proximal end of the metaphyseal portion abuts the flange portion;
wherein the metaphyseal portion includes a first concavity having a surface for receiving at least a part of a greater tuberosity of the patient and a second concavity having a surface for receiving at least a part of a lesser tuberosity of the patient;
wherein the first concavity is defined at least in part by at least a portion of the first opposed surface of the fin element extending from the body of the metaphyseal portion;
wherein the second concavity is defined at least in part by at least a portion of the second opposed surface of the fin element extending from the body of the metaphyseal portion;
wherein the first concavity and the second concavity are asymmetric; and
wherein a position of a free edge of the fin substantially mimics a position of essentially an entire three-dimensional anatomical location of a bicipital groove.

19. The shoulder prosthesis of claim 18, wherein the free edge of the fin substantially mimics the position of essentially the entire three-dimensional anatomical location of the bicipital groove along a centerline of the bicipital groove.

20. The shoulder prosthesis of claim 19, wherein an offset distance of a point on the free edge of the fin from a centerline of the shaft portion varies with the vertical location of the point on the free edge of the fin.

21. The shoulder prosthesis of claim 18, wherein a thickness of the fin decreases as a function of distance from the body of the metaphyseal portion.

22. The shoulder prosthesis of claim 18, wherein the fin defines a first tuberosity receiving portion configured to receive essentially the entire greater tuberosity and a second tuberosity receiving portion configured to receive essentially the entire lesser tuberosity.

23. The shoulder prosthesis of claim 22, wherein the first tuberosity receiving portion is configured to receive essentially the entire greater tuberosity without removal of substantial bone mass therefrom and the second tuberosity receiving portion is configured to receive essentially the entire lesser tuberosity without removal of substantial bone mass therefrom.

24. The shoulder prosthesis of claim 22, wherein the first tuberosity receiving portion is configured to receive essentially the entire greater tuberosity without substantially changing the shape thereof and the second tuberosity receiving portion is configured to receive essentially the entire lesser tuberosity without substantially changing the shape thereof.

25. The shoulder prosthesis of claim 22, wherein the first tuberosity receiving portion has an elongated shape and the second tuberosity receiving portion has an elongated shape.

26. The shoulder prosthesis of claim 18, further comprising a prosthetic humeral head.

27. The shoulder prosthesis of claim 26, wherein the prosthetic humeral head is attached to the flange portion.

28. The shoulder prosthesis of claim 27, wherein the prosthetic humeral head is attached to the flange portion via a Morse Taper.

29. The shoulder prosthesis of claim 28, wherein the Morse Taper is offset from center in a posterior direction.

30. The shoulder prosthesis of claim 18, wherein the flange includes at least one hole for receiving a suture.

31. The shoulder prosthesis of claim 18, wherein the shaft portion is adapted to be anchored in a medullary canal of the humerus shaft.

32. The shoulder prosthesis of claim 31, wherein the shaft portion includes at least one groove for gripping the medullary canal of the humerus shaft.

33. The shoulder prosthesis of claim 18, wherein the fin has at least one aperture therethrough.

34. The shoulder prosthesis of claim 33, wherein the aperture is selected from the group including: (a) a suture hole for receiving a suture; and (b) a window through which osseous fusion may occur.

* * * * *